(12) United States Patent
Atiya et al.

(10) Patent No.: US 10,456,043 B2
(45) Date of Patent: Oct. 29, 2019

(54) COMPACT CONFOCAL DENTAL SCANNING APPARATUS

(71) Applicant: Align Technology, Inc., San Jose, CA (US)

(72) Inventors: Yossef Atiya, Maccabim (IL); Tal Verker, Ofra (IL)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 15/859,010

(22) Filed: Dec. 29, 2017

(65) Prior Publication Data

US 2018/0192877 A1 Jul. 12, 2018

Related U.S. Application Data

(60) Provisional application No. 62/445,663, filed on Jan. 12, 2017.

(51) Int. Cl.
*G01B 11/24* (2006.01)
*A61B 5/00* (2006.01)
(Continued)

(52) U.S. Cl.
CPC ............ *A61B 5/0068* (2013.01); *A61B 1/247* (2013.01); *A61B 5/0088* (2013.01); *A61C 7/002* (2013.01);
(Continued)

(58) Field of Classification Search
CPC .......... G01N 2035/00326; G01N 2035/00495; G01N 35/0092; G01N 2015/1006; G01N 35/026; G01N 35/10; G01N 35/00; G01N 35/00871; G01N 35/1065; G01N 21/25; G01N 33/54366; G01N 15/1475; G01N 2035/00138; G01N 2035/00356; G01N 2035/00366; G01N 2035/00425; G01N 2035/0449; G01N 2035/0486; G01N 2035/0491; G01N 2201/024;
(Continued)

(56) References Cited

U.S. PATENT DOCUMENTS

| 2,171,695 A | 9/1939 | Harper |
| 2,467,432 A | 4/1949 | Kesling |

(Continued)

FOREIGN PATENT DOCUMENTS

| AU | 517102 B | 11/1977 |
| AU | 3031677 A | 11/1977 |

(Continued)

OTHER PUBLICATIONS

US 8,553,966 B1, 10/2013, Alpern et al. (withdrawn)

(Continued)

*Primary Examiner* — Michael P Stafira
(74) *Attorney, Agent, or Firm* — Lowenstein Sandler LLP

(57) ABSTRACT

Described herein are apparatuses and methods for confocal 3D scanning. The apparatus can comprise a spatial pattern disposed on a transparent base and a light source configured to provide illumination to the spatial pattern and an optical system comprising projection/imaging optics having one or more lenses and an optical axis. The projecting/imaging optics may be scanned to provide depth scanning by moving along the optical axis.

46 Claims, 8 Drawing Sheets

(51) Int. Cl.
*A61C 7/00* (2006.01)
*A61C 9/00* (2006.01)
*G02B 21/00* (2006.01)
*A61B 1/247* (2006.01)
*G02B 21/36* (2006.01)
*G01B 11/06* (2006.01)
*A61C 19/04* (2006.01)

(52) U.S. Cl.
CPC ............ *A61C 9/006* (2013.01); *A61C 9/0066* (2013.01); *G01B 11/0608* (2013.01); *G01B 11/24* (2013.01); *G02B 21/0024* (2013.01); *G02B 21/0028* (2013.01); *G02B 21/367* (2013.01); *A61B 5/7246* (2013.01); *A61C 19/04* (2013.01)

(58) Field of Classification Search
CPC ......... G01N 2201/04; G01N 35/00029; G01N 35/00069; G01N 35/04; G01N 35/1011; G01N 35/1072; G01N 2015/0073; G01N 2015/008; G01N 2015/1486; G01N 2035/00148; G01N 2035/00237; G01N 2035/00306; G01N 2035/00435; G01N 2035/00633; G01N 2035/0474; G01N 2035/0493; G01N 2035/0494; G01N 21/27; G01N 2201/12; G01N 33/5005; G01N 33/54306; G01N 33/54313; G01N 33/56983; G01N 35/62; G01N 33/6827; G01N 33/80; G01N 33/92; G01N 35/00623; G01N 35/1009; G01N 21/76; G01N 1/30; G01N 21/6428; G01N 21/78; G01N 2035/103; G01N 21/75; G01N 33/50; G01N 15/14; G01N 1/28; G01N 2021/825; G01N 2035/00881; G01N 2035/0094; G01N 21/21; G01N 21/35; G01N 21/4133; G01N 21/645; G01N 21/65; G01N 33/5302; G01N 35/0098; G01N 15/0272; G01N 15/1484; G01N 2015/0092; G01N 2021/513; G01N 2021/6417; G01N 2021/6441; G01N 2035/00277; G01N 2035/00811; G01N 2035/1034; G01N 21/07; G01N 21/51; G01N 21/84; G01N 35/00732; G01N 1/08; G01N 1/31; G01N 1/38; G01N 1/40; G01N 1/4077; G01N 2001/002; G01N 2001/4083; G01N 2021/458; G01N 2021/6439; G01N 2021/6478; G01N 2021/6482; G01N 2021/758; G01N 2021/7786; G01N 2030/8827; G01N 2033/0078; G01N 2035/1048; G01N 21/0303; G01N 21/4795; G01N 21/64; G01N 21/643; G01N 21/6452; G01N 21/66; G01N 2333/705; G01N 2333/948; G01N 2500/04; G01N 27/745; G01N 2800/50; G01N 2800/52; G01N 2800/56; G01N 2800/7028; G01N 30/02; G01N 30/88; G01N 31/222; G01N 33/00; G01N 33/48; G01N 33/4833; G01N 33/5011; G01N 33/52; G01N 33/56; G01N 33/533; G01N 33/54393; G01N 33/559; G01N 33/566; G01N 33/56911; G01N 33/56938; G01N 33/573; G01N 33/57496; G01N 33/58; G01N 33/582; G01N 33/585; G01N 33/86; G01N 35/02; G01N 35/1095; G02B 1/14; G02B 21/16; G02B 21/34; G02B 3/0056; G02B 5/005; G02B 5/305; G02B 17/002; G02B 17/06; G02B 17/061; G02B 17/0808; G02B 17/086; G02B 1/10; G02B 1/11; G02B 21/0024; G02B 21/0028; G02B 21/0056; G02B 21/04; G02B 21/06; G02B 21/33; G02B 21/365; G02B 21/367; G02B 23/243; G02B 23/2453; G02B 23/2469; G02B 23/2476; G02B 21/101; G02B 27/0927; G02B 27/2292; G02B 27/56; G02B 3/0006; G02B 3/0081; G02B 5/3033; G02B 5/3083; G02B 6/005; G02B 6/0065; G01B 11/0608; G01B 11/24; G01B 9/02004; G01B 9/0203; G01B 9/02032; G01B 9/02043; G01B 9/02044; G01B 9/02072; G01B 9/02077; G01B 9/02085; G01B 9/02091; G01B 9/02097

See application file for complete search history.

(56) References Cited

U.S. PATENT DOCUMENTS

| | | |
|---|---|---|
| 2,531,222 A | 11/1950 | Kesling |
| 3,379,193 A | 4/1968 | Monsghan |
| 3,385,291 A | 5/1968 | Martin |
| 3,407,500 A | 10/1968 | Kesling |
| 3,478,742 A | 11/1969 | Bohlmann |
| 3,496,936 A | 2/1970 | Gores |
| 3,533,163 A | 10/1970 | Kirschenbaum |
| 3,556,093 A | 1/1971 | Quick |
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,255,138 A | 3/1981 | Frohn |
| 4,324,546 A | 4/1982 | Heitlinger et al. |
| 4,324,547 A | 4/1982 | Arcan et al. |
| 4,348,178 A | 9/1982 | Kurz |
| 4,419,992 A | 12/1983 | Chorbajian |
| 4,433,956 A | 2/1984 | Witzig |
| 4,478,580 A | 10/1984 | Barrut |
| 4,500,294 A | 2/1985 | Lewis |
| 4,505,673 A | 3/1985 | Yoshii |
| 4,519,386 A | 5/1985 | Sullivan |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,755,139 A | 7/1988 | Abbatte et al. |
| 4,757,824 A | 7/1988 | Chaumet |
| 4,763,791 A | 8/1988 | Halverson et al. |
| 4,764,111 A | 8/1988 | Knierim |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |

(56) References Cited

U.S. PATENT DOCUMENTS

| | | |
|---|---|---|
| 4,877,398 A | 10/1989 | Kesling |
| 4,880,380 A | 11/1989 | Martz |
| 4,886,451 A | 12/1989 | Cetlin |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,928 A | 8/1990 | Carroll et al. |
| 4,964,770 A | 10/1990 | Steinbichler et al. |
| 4,975,052 A | 12/1990 | Spencer et al. |
| 4,983,334 A | 1/1991 | Adell |
| 4,997,369 A | 3/1991 | Shafir |
| 5,002,485 A | 3/1991 | Aagesen |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,037,295 A | 8/1991 | Bergersen |
| 5,055,039 A | 10/1991 | Abbatte et al. |
| 5,100,316 A | 3/1992 | Wildman |
| 5,103,838 A | 4/1992 | Yousif |
| 5,121,333 A | 6/1992 | Riley et al. |
| 5,123,425 A | 6/1992 | Shannon et al. |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,204,670 A | 4/1993 | Stinton |
| 5,242,304 A | 9/1993 | Truax et al. |
| 5,245,592 A | 9/1993 | Kuemmel et al. |
| 5,273,429 A | 12/1993 | Rekow et al. |
| 5,278,756 A | 1/1994 | Lemchen et al. |
| 5,306,144 A | 4/1994 | Hibst et al. |
| 5,328,362 A | 7/1994 | Watson et al. |
| 5,335,657 A | 8/1994 | Terry et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,372,502 A | 12/1994 | Massen et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,499,633 A | 3/1996 | Fenton |
| 5,528,735 A | 6/1996 | Strasnick et al. |
| 5,533,895 A | 7/1996 | Andreiko et al. |
| 5,540,732 A | 7/1996 | Testerman |
| 5,542,842 A | 8/1996 | Andreiko et al. |
| 5,543,780 A | 8/1996 | McAuley et al. |
| 5,549,476 A | 8/1996 | Stern |
| 5,562,448 A | 10/1996 | Mushabac |
| 5,570,182 A | 10/1996 | Nathel et al. |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,626,537 A | 5/1997 | Danyo et al. |
| 5,645,420 A | 7/1997 | Bergersen |
| 5,645,421 A | 7/1997 | Slootsky |
| 5,651,671 A | 7/1997 | Seay et al. |
| 5,655,653 A | 8/1997 | Chester |
| 5,659,420 A | 8/1997 | Wakai et al. |
| 5,683,243 A | 11/1997 | Andreiko et al. |
| 5,683,244 A | 11/1997 | Truax |
| 5,691,539 A | 11/1997 | Pfeiffer |
| 5,692,894 A | 12/1997 | Schwartz et al. |
| 5,725,376 A | 3/1998 | Poirier |
| 5,725,378 A | 3/1998 | Wang |
| 5,737,084 A | 4/1998 | Ishihara |
| 5,740,267 A | 4/1998 | Echerer et al. |
| 5,742,700 A | 4/1998 | Yoon et al. |
| 5,769,631 A | 6/1998 | Williams |
| 5,774,425 A | 6/1998 | Ivanov et al. |
| 5,790,242 A | 8/1998 | Stern et al. |
| 5,799,100 A | 8/1998 | Clarke et al. |
| 5,800,174 A | 9/1998 | Andersson |
| 5,816,800 A | 10/1998 | Brehm et al. |
| 5,818,587 A | 10/1998 | Devaraj et al. |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,904,479 A | 5/1999 | Staples |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 5,980,246 A | 11/1999 | Ramsay et al. |
| 5,989,023 A | 11/1999 | Summer et al. |
| 6,044,309 A | 3/2000 | Honda |
| 6,049,743 A | 4/2000 | Baba |
| 6,053,731 A | 4/2000 | Heckenberger |
| 6,068,482 A | 5/2000 | Snow |
| 6,099,303 A | 8/2000 | Gibbs et al. |
| 6,099,314 A | 8/2000 | Kopelman et al. |
| 6,123,544 A | 9/2000 | Cleary |
| 6,152,731 A | 11/2000 | Jordan et al. |
| 6,154,676 A | 11/2000 | Levine |
| 6,183,248 B1 | 2/2001 | Chishti et al. |
| 6,186,780 B1 | 2/2001 | Hibst et al. |
| 6,190,165 B1 | 2/2001 | Andreiko et al. |
| 6,200,133 B1 | 3/2001 | Kittelsen |
| 6,201,880 B1 | 3/2001 | Elbaum et al. |
| 6,212,435 B1 | 4/2001 | Lattner et al. |
| 6,217,334 B1 | 4/2001 | Hultgren |
| 6,231,338 B1 | 5/2001 | de Josselin de Jong et al. |
| 6,239,705 B1 | 5/2001 | Glen |
| 6,243,601 B1 | 6/2001 | Wist |
| 6,263,234 B1 | 7/2001 | Engelhardt et al. |
| 6,299,438 B1 | 10/2001 | Sahagian et al. |
| 6,300,215 B1 | 10/2001 | Phan et al. |
| 6,315,553 B1 | 11/2001 | Sachdeva et al. |
| 6,328,745 B1 | 12/2001 | Ascherman |
| 6,334,073 B1 | 12/2001 | Levine |
| 6,350,120 B1 | 2/2002 | Sachdeva et al. |
| 6,364,660 B1 | 4/2002 | Durbin et al. |
| 6,382,975 B1 | 5/2002 | Poirier |
| 6,402,510 B1 | 6/2002 | Williams |
| 6,402,707 B1 | 6/2002 | Ernst |
| 6,405,729 B1 | 6/2002 | Thornton |
| 6,436,058 B1 | 8/2002 | Krahner et al. |
| 6,450,807 B1 | 9/2002 | Chishti et al. |
| 6,482,298 B1 | 11/2002 | Bhatnagar |
| 6,499,995 B1 | 12/2002 | Schwartz |
| 6,515,593 B1 | 2/2003 | Stark et al. |
| 6,516,805 B1 | 2/2003 | Thornton |
| 6,520,772 B2 | 2/2003 | Williams |
| 6,524,101 B1 | 2/2003 | Phan et al. |
| 6,540,707 B1 | 4/2003 | Stark et al. |
| 6,572,372 B1 | 6/2003 | Phan et al. |
| 6,573,998 B2 | 6/2003 | Cohen Sabban |
| 6,594,539 B1 | 7/2003 | Geng |
| 6,597,934 B1 | 7/2003 | de Jong et al. |
| 6,602,070 B2 | 8/2003 | Miller et al. |
| 6,611,783 B2 | 8/2003 | Kelly et al. |
| 6,613,001 B1 | 9/2003 | Dworkin |

(56) References Cited

U.S. PATENT DOCUMENTS

| | | |
|---|---|---|
| 6,616,579 B1 | 9/2003 | Reinbold et al. |
| 6,623,698 B2 | 9/2003 | Kuo |
| 6,624,752 B2 | 9/2003 | Klitsgaard et al. |
| 6,626,180 B1 | 9/2003 | Kittelsen et al. |
| 6,640,128 B2 | 10/2003 | Vilsmeier et al. |
| 6,697,164 B1 | 2/2004 | Babayoff et al. |
| 6,702,765 B2 | 3/2004 | Robbins et al. |
| 6,702,804 B1 | 3/2004 | Ritter et al. |
| 6,705,863 B2 | 3/2004 | Phan et al. |
| 6,830,450 B2 | 12/2004 | Knopp et al. |
| 6,885,464 B1 | 4/2005 | Pfeiffer et al. |
| 6,890,285 B2 | 5/2005 | Rahman et al. |
| 7,036,514 B2 | 5/2006 | Heck |
| 7,092,107 B2 | 8/2006 | Babayoff et al. |
| 7,106,233 B2 | 9/2006 | Schroeder et al. |
| 7,112,065 B2 | 9/2006 | Kopelman et al. |
| 7,121,825 B2 | 10/2006 | Chishti et al. |
| 7,138,640 B1 | 11/2006 | Delgado et al. |
| 7,142,312 B2 | 11/2006 | Quadling et al. |
| 7,166,063 B2 | 1/2007 | Rahman et al. |
| 7,184,150 B2 | 2/2007 | Quadling et al. |
| 7,192,273 B2 | 3/2007 | McSurdy |
| 7,220,124 B2 | 5/2007 | Taub et al. |
| 7,286,954 B2 | 10/2007 | Kopelman et al. |
| 7,292,759 B2 | 11/2007 | Boutoussov et al. |
| 7,302,842 B2 | 12/2007 | Biester et al. |
| 7,338,327 B2 | 3/2008 | Sticker et al. |
| D565,509 S | 4/2008 | Fechner et al. |
| 7,351,116 B2 | 4/2008 | Dold |
| 7,357,637 B2 | 4/2008 | Liechtung |
| 7,450,231 B2 | 11/2008 | Johs et al. |
| 7,458,810 B2 | 12/2008 | Bergersen |
| 7,460,230 B2 | 12/2008 | Johs et al. |
| 7,462,076 B2 | 12/2008 | Walter et al. |
| 7,463,929 B2 | 12/2008 | Simmons |
| 7,500,851 B2 | 3/2009 | Williams |
| D594,413 S | 6/2009 | Palka et al. |
| 7,544,103 B2 | 6/2009 | Walter et al. |
| 7,553,157 B2 | 6/2009 | Abolfathi et al. |
| 7,561,273 B2 | 7/2009 | Stautmeister et al. |
| 7,577,284 B2 | 8/2009 | Wong et al. |
| 7,596,253 B2 | 9/2009 | Wong et al. |
| 7,597,594 B2 | 10/2009 | Stadler et al. |
| 7,609,875 B2 | 10/2009 | Liu et al. |
| D603,796 S | 11/2009 | Sticker et al. |
| 7,616,319 B1 | 11/2009 | Woollam et al. |
| 7,626,705 B2 | 12/2009 | Altendorf |
| 7,632,216 B2 | 12/2009 | Rahman et al. |
| 7,633,625 B1 | 12/2009 | Woollam et al. |
| 7,637,262 B2 | 12/2009 | Bailey |
| 7,668,355 B2 | 2/2010 | Wong et al. |
| 7,670,179 B2 | 3/2010 | Müller |
| 7,695,327 B2 | 4/2010 | Bäuerle et al. |
| 7,698,068 B2 | 4/2010 | Babayoff |
| 7,724,378 B2 | 5/2010 | Babayoff |
| D618,619 S | 6/2010 | Walter |
| 7,731,508 B2 | 6/2010 | Borst |
| 7,735,217 B2 | 6/2010 | Borst |
| 7,780,460 B2 | 8/2010 | Walter |
| 7,787,132 B2 | 8/2010 | Körner et al. |
| 7,791,810 B2 | 9/2010 | Powell |
| 7,796,243 B2 | 9/2010 | Choo-Smith et al. |
| 7,806,727 B2 | 10/2010 | Dold et al. |
| 7,813,787 B2 | 10/2010 | de Josselin de Jong et al. |
| 7,824,180 B2 | 11/2010 | Abolfathi et al. |
| 7,828,601 B2 | 11/2010 | Pyczak |
| 7,845,969 B2 | 12/2010 | Stadler et al. |
| 7,854,609 B2 | 12/2010 | Chen et al. |
| 7,862,336 B2 | 1/2011 | Kopelman et al. |
| 7,872,760 B2 | 1/2011 | Ertl |
| 7,874,836 B2 | 1/2011 | McSurdy |
| 7,874,849 B2 | 1/2011 | Sticker et al. |
| 7,878,801 B2 | 2/2011 | Abolfathi et al. |
| 7,907,280 B2 | 3/2011 | Johs et al. |
| 7,929,151 B2 | 4/2011 | Mang et al. |
| 7,947,508 B2 | 5/2011 | Tricca et al. |
| 7,959,308 B2 | 6/2011 | Freeman et al. |
| 7,963,766 B2 | 6/2011 | Cronauer |
| 7,986,415 B2 | 7/2011 | Thiel et al. |
| 8,017,891 B2 | 9/2011 | Nevin |
| 8,026,916 B2 | 9/2011 | Wen |
| 8,027,709 B2 | 9/2011 | Arnone et al. |
| 8,054,556 B2 | 11/2011 | Chen et al. |
| 8,077,949 B2 | 12/2011 | Liang et al. |
| 8,083,556 B2 | 12/2011 | Stadler et al. |
| D652,799 S | 1/2012 | Mueller |
| 8,118,592 B2 | 2/2012 | Tortorici |
| 8,126,025 B2 | 2/2012 | Takeda |
| 8,144,954 B2 | 3/2012 | Quadling et al. |
| 8,160,334 B2 | 4/2012 | Thiel et al. |
| 8,201,560 B2 | 6/2012 | Dembro |
| 8,215,312 B2 | 7/2012 | Garabadian et al. |
| 8,240,018 B2 | 8/2012 | Walter et al. |
| 8,279,450 B2 | 10/2012 | Oota et al. |
| 8,292,617 B2 | 10/2012 | Brandt et al. |
| 8,294,657 B2 | 10/2012 | Kim et al. |
| 8,297,286 B2 | 10/2012 | Smernoff |
| 8,306,608 B2 | 11/2012 | Mandelis et al. |
| 8,310,683 B2 | 11/2012 | Babayoff et al. |
| 8,314,764 B2 | 11/2012 | Kim et al. |
| 8,332,015 B2 | 12/2012 | Ertl |
| 8,354,588 B2 | 1/2013 | Sticker et al. |
| 8,363,228 B2 | 1/2013 | Babayoff |
| 8,366,479 B2 | 2/2013 | Borst et al. |
| 8,465,280 B2 | 6/2013 | Sachdeva et al. |
| 8,477,320 B2 | 7/2013 | Stock et al. |
| 8,488,113 B2 | 7/2013 | Thiel et al. |
| 8,520,922 B2 | 8/2013 | Wang et al. |
| 8,520,925 B2 | 8/2013 | Duret et al. |
| 8,556,625 B2 | 10/2013 | Lovely |
| 8,570,530 B2 | 10/2013 | Liang |
| 8,573,224 B2 | 11/2013 | Thornton |
| 8,577,212 B2 | 11/2013 | Thiel |
| 8,594,408 B2 | 11/2013 | Alpern et al. |
| 8,650,586 B2 | 2/2014 | Lee et al. |
| 8,675,706 B2 | 3/2014 | Seurin et al. |
| 8,723,029 B2 | 5/2014 | Pyczak et al. |
| 8,743,923 B2 | 6/2014 | Geske et al. |
| 8,767,270 B2 | 7/2014 | Curry et al. |
| 8,768,016 B2 | 7/2014 | Pan et al. |
| 8,771,149 B2 | 7/2014 | Rahman et al. |
| 8,839,476 B2 | 9/2014 | Adachi |
| 8,870,566 B2 | 10/2014 | Bergersen |
| 8,878,905 B2 | 11/2014 | Fisker et al. |
| 8,899,976 B2 | 12/2014 | Chen et al. |
| 8,936,463 B2 | 1/2015 | Mason et al. |
| 8,948,482 B2 | 2/2015 | Levin |
| 8,956,058 B2 | 2/2015 | Rosch |
| 8,992,216 B2 | 3/2015 | Karazivan |
| 9,022,792 B2 | 5/2015 | Sticker et al. |
| 9,039,418 B1 | 5/2015 | Rubbert |
| 9,084,535 B2 | 7/2015 | Girkin et al. |
| 9,108,338 B2 | 8/2015 | Sirovskiy et al. |
| 9,144,512 B2 | 9/2015 | Wagner |
| 9,192,305 B2 | 11/2015 | Levin |
| 9,204,952 B2 | 12/2015 | Lampalzer |
| 9,242,118 B2 | 1/2016 | Brawn |
| 9,261,358 B2 | 2/2016 | Atiya et al. |
| 9,299,192 B2 | 3/2016 | Kopelman |
| 9,336,336 B2 | 5/2016 | Deichmann et al. |
| 9,408,743 B1 | 8/2016 | Wagner |
| 9,433,476 B2 | 9/2016 | Khardekar et al. |
| 9,439,568 B2 | 9/2016 | Atiya et al. |
| 9,444,981 B2 | 9/2016 | Bellis et al. |
| 9,500,635 B2 | 11/2016 | Islam |
| 9,506,808 B2 | 11/2016 | Jeon et al. |
| 9,513,470 B1 † | 12/2016 | Weaver |
| 9,545,331 B2 | 1/2017 | Ingemarsson-Matzen |
| 9,584,771 B2 | 2/2017 | Mandelis et al. |
| 9,675,430 B2 | 6/2017 | Verker et al. |
| 9,693,839 B2 | 7/2017 | Atiya et al. |
| 9,744,006 B2 | 8/2017 | Ross |
| 9,936,186 B2 | 4/2018 | Jesenko et al. |
| 2001/0038705 A1 | 11/2001 | Rubbert et al. |

(56) References Cited

U.S. PATENT DOCUMENTS

| | | |
|---|---|---|
| 2002/0010568 A1 | 1/2002 | Rubbert et al. |
| 2002/0015934 A1 | 2/2002 | Rubbert et al. |
| 2003/0009252 A1 | 1/2003 | Pavlovskaia et al. |
| 2003/0048540 A1 | 3/2003 | Xie et al. |
| 2003/0139834 A1 | 7/2003 | Nikolskiy et al. |
| 2003/0190575 A1 | 10/2003 | Hilliard |
| 2003/0207224 A1 | 11/2003 | Lotte |
| 2003/0224311 A1 | 12/2003 | Cronauer |
| 2004/0009449 A1 | 1/2004 | Mah et al. |
| 2004/0019262 A1 | 1/2004 | Perelgut |
| 2004/0058295 A1 | 3/2004 | Bergersen |
| 2004/0090638 A1 | 5/2004 | Babayoff et al. |
| 2004/0094165 A1 | 5/2004 | Cook |
| 2005/0031196 A1 | 2/2005 | Moghaddam et al. |
| 2005/0037312 A1 | 2/2005 | Uchida |
| 2005/0048433 A1 | 3/2005 | Hilliard |
| 2005/0100333 A1 | 5/2005 | Kerschbaumer et al. |
| 2005/0181333 A1 | 8/2005 | Karazivan et al. |
| 2005/0186524 A1 | 8/2005 | Abolfathi et al. |
| 2005/0244781 A1 | 11/2005 | Abels et al. |
| 2006/0084024 A1 | 4/2006 | Farrell |
| 2006/0099546 A1 | 5/2006 | Bergersen |
| 2006/0154198 A1 | 7/2006 | Durbin et al. |
| 2006/0223032 A1 | 10/2006 | Fried et al. |
| 2006/0223342 A1 | 10/2006 | Borst et al. |
| 2006/0234179 A1 | 10/2006 | Wen et al. |
| 2007/0046865 A1 | 3/2007 | Umeda et al. |
| 2007/0053048 A1 | 3/2007 | Kumar et al. |
| 2007/0087300 A1 | 4/2007 | Willison et al. |
| 2007/0184402 A1 | 8/2007 | Boutoussov et al. |
| 2007/0231765 A1 | 10/2007 | Phan et al. |
| 2007/0296959 A1 | 12/2007 | Schwotzer |
| 2008/0045053 A1 | 2/2008 | Stadler et al. |
| 2008/0063998 A1 | 3/2008 | Liang et al. |
| 2008/0090208 A1 | 4/2008 | Rubbert |
| 2008/0115791 A1 | 5/2008 | Heine |
| 2008/0176448 A1 | 7/2008 | Muller et al. |
| 2008/0242144 A1 | 10/2008 | Dietz |
| 2009/0030347 A1 | 1/2009 | Cao |
| 2009/0040740 A1 | 2/2009 | Muller et al. |
| 2009/0061379 A1 | 3/2009 | Yamamoto et al. |
| 2009/0061381 A1 | 3/2009 | Durbin et al. |
| 2009/0075228 A1 | 3/2009 | Kaneko et al. |
| 2009/0210032 A1 | 8/2009 | Beiski et al. |
| 2009/0218514 A1 | 9/2009 | Klunder et al. |
| 2009/0298017 A1 | 12/2009 | Boerjes et al. |
| 2009/0305540 A1 | 12/2009 | Stadler et al. |
| 2010/0045902 A1 | 2/2010 | Ikeda et al. |
| 2010/0085636 A1† | 4/2010 | Berner |
| 2010/0152599 A1 | 6/2010 | DuHamel et al. |
| 2010/0165275 A1 | 7/2010 | Tsukamoto et al. |
| 2010/0167225 A1 | 7/2010 | Kuo |
| 2010/0231577 A1 | 9/2010 | Kim et al. |
| 2010/0312484 A1 | 12/2010 | DuHamel et al. |
| 2011/0045428 A1 | 2/2011 | Boltunov et al. |
| 2011/0081625 A1 | 4/2011 | Fuh |
| 2011/0102549 A1 | 5/2011 | Takahashi |
| 2011/0102566 A1 | 5/2011 | Zakian et al. |
| 2011/0143673 A1 | 6/2011 | Landesman et al. |
| 2011/0229840 A1 | 9/2011 | Liang et al. |
| 2011/0235045 A1 | 9/2011 | Koerner et al. |
| 2011/0269092 A1 | 11/2011 | Kuo et al. |
| 2012/0081786 A1 | 4/2012 | Mizuyama et al. |
| 2012/0086681 A1 | 4/2012 | Kim et al. |
| 2012/0092461 A1 | 4/2012 | Fisker et al. |
| 2012/0129117 A1 | 5/2012 | McCance |
| 2012/0147912 A1 | 6/2012 | Moench et al. |
| 2012/0172678 A1 | 7/2012 | Logan et al. |
| 2012/0281293 A1 | 11/2012 | Gronenborn et al. |
| 2012/0295216 A1 | 11/2012 | Dykes et al. |
| 2012/0322025 A1 | 12/2012 | Ozawa et al. |
| 2013/0089828 A1 | 4/2013 | Borovinskih et al. |
| 2013/0095446 A1 | 4/2013 | Andreiko et al. |
| 2013/0103176 A1 | 4/2013 | Kopelman et al. |
| 2013/0110469 A1 | 5/2013 | Kopelman |
| 2013/0163627 A1 | 6/2013 | Seurin et al. |
| 2013/0201488 A1 | 8/2013 | Ishihara |
| 2013/0235165 A1 | 9/2013 | Gharib et al. |
| 2013/0252195 A1 | 9/2013 | Popat |
| 2013/0266326 A1 | 10/2013 | Joseph et al. |
| 2013/0280671 A1 | 10/2013 | Brawn et al. |
| 2013/0286174 A1 | 10/2013 | Urakabe |
| 2013/0293824 A1 | 11/2013 | Yoneyama et al. |
| 2013/0323664 A1 | 12/2013 | Parker |
| 2013/0323671 A1 | 12/2013 | Dillon et al. |
| 2013/0323674 A1 | 12/2013 | Hakomori et al. |
| 2014/0081091 A1 | 3/2014 | Abolfathi et al. |
| 2014/0272774 A1 | 9/2014 | Dillon et al. |
| 2014/0294273 A1 | 10/2014 | Jaisson |
| 2014/0313299 A1 | 10/2014 | Gebhardt et al. |
| 2014/0329194 A1 | 11/2014 | Sachdeva et al. |
| 2014/0363778 A1 | 12/2014 | Parker |
| 2015/0002649 A1 | 1/2015 | Nowak et al. |
| 2015/0029309 A1 | 1/2015 | Michaeli et al. |
| 2015/0079531 A1 | 3/2015 | Heine |
| 2015/0140502 A1 | 5/2015 | Brawn et al. |
| 2015/0164335 A1 | 6/2015 | Van Der Poel et al. |
| 2015/0173856 A1 | 6/2015 | Iowe et al. |
| 2015/0230885 A1 | 8/2015 | Wucher |
| 2015/0238280 A1 | 8/2015 | Wu et al. |
| 2015/0238283 A1 | 8/2015 | Tanugula et al. |
| 2015/0306486 A1 | 10/2015 | Logan et al. |
| 2015/0320320 A1 | 11/2015 | Kopelman et al. |
| 2015/0325044 A1 | 11/2015 | Lebovitz |
| 2015/0338209 A1 | 11/2015 | Knottel |
| 2016/0000332 A1 | 1/2016 | Atiya et al. |
| 2016/0003610 A1 | 1/2016 | Lampert et al. |
| 2016/0045291 A1 | 2/2016 | Verker et al. |
| 2016/0051345 A1 | 2/2016 | Levin |
| 2016/0064898 A1 | 3/2016 | Atiya et al. |
| 2016/0067013 A1 | 3/2016 | Morton et al. |
| 2016/0081768 A1 | 3/2016 | Kopelman et al. |
| 2016/0081769 A1 | 3/2016 | Kimura et al. |
| 2016/0135924 A1 | 5/2016 | Choi et al. |
| 2016/0135925 A1 | 5/2016 | Mason et al. |
| 2016/0163115 A1 | 6/2016 | Furst |
| 2016/0217708 A1 | 7/2016 | Levin et al. |
| 2016/0296303 A1 | 10/2016 | Parker |
| 2016/0328843 A1 | 11/2016 | Graham et al. |
| 2016/0330355 A1† | 11/2016 | Tchouprakov |
| 2017/0007366 A1 | 1/2017 | Kopelman et al. |
| 2017/0007367 A1 | 1/2017 | Li et al. |
| 2017/0049311 A1 | 2/2017 | Borovinskih et al. |
| 2017/0049326 A1 | 2/2017 | Alfano et al. |
| 2017/0056131 A1 | 3/2017 | Alauddin et al. |
| 2017/0156821 A1 | 6/2017 | Kopelman et al. |
| 2017/0265970 A1 | 9/2017 | Verker |
| 2017/0325690 A1 | 11/2017 | Salah et al. |
| 2018/0000563 A1 | 1/2018 | Shanjani et al. |
| 2018/0000565 A1 | 1/2018 | Shanjani et al. |
| 2018/0028063 A1 | 2/2018 | Elbaz et al. |
| 2018/0028064 A1 | 2/2018 | Elbaz et al. |
| 2018/0028065 A1 | 2/2018 | Elbaz et al. |
| 2018/0055602 A1 | 3/2018 | Kopelman et al. |
| 2018/0125610 A1 | 5/2018 | Carrier, Jr. et al. |
| 2018/0153648 A1 | 6/2018 | Shanjani et al. |
| 2018/0153649 A1 | 6/2018 | Wu et al. |
| 2018/0153733 A1 | 6/2018 | Kuo |
| 2018/0280118 A1 | 10/2018 | Cramer |
| 2018/0284727 A1 | 10/2018 | Cramer et al. |

FOREIGN PATENT DOCUMENTS

| | | |
|---|---|---|
| AU | 9150082 A | 6/1984 |
| AU | 5598894 A | 6/1994 |
| CA | 1121955 A1 | 4/1982 |
| CN | 102802520 A | 11/2012 |
| DE | 2749802 A1 | 5/1978 |
| DE | 69327661 T2 | 7/2000 |
| DE | 102005043627 A1 | 3/2007 |
| DE | 202010017014 U1 | 3/2011 |
| DE | 102011051443 A1 | 1/2013 |
| DE | 102014225457 A1 | 6/2016 |
| EP | 0428152 A1 | 5/1991 |

(56) References Cited

FOREIGN PATENT DOCUMENTS

| | | |
|---|---|---|
| EP | 490848 A2 | 6/1992 |
| EP | 541500 A1 | 5/1993 |
| EP | 714632 B1 | 5/1997 |
| EP | 774933 B1 | 12/2000 |
| EP | 731673 B1 | 5/2001 |
| EP | 1941843 A2 | 7/2008 |
| EP | 2213223 A1 | 8/2010 |
| EP | 2437027 A2 | 4/2012 |
| EP | 2447754 A1 | 5/2012 |
| EP | 1989764 B1 | 7/2012 |
| EP | 2332221 B1 | 11/2012 |
| EP | 2596553 B1 | 12/2013 |
| EP | 2612300 B1 | 2/2015 |
| EP | 2848229 A1 | 3/2015 |
| ES | 463897 A1 | 1/1980 |
| ES | 2455066 A1 | 4/2014 |
| FR | 2369828 A1 | 6/1978 |
| FR | 2930334 A1 | 10/2009 |
| GB | 1550777 A | 8/1979 |
| JP | 53-058191 A | 5/1978 |
| JP | 40238359 A | 1/1992 |
| JP | 08-508174 A | 9/1996 |
| JP | 2002-522752 A | 7/2002 |
| JP | 2003290133 A | 10/2003 |
| JP | 2007260158 A | 10/2007 |
| JP | 2008523370 A | 7/2008 |
| JP | 04184427 B1 | 11/2008 |
| JP | 2009000412 A | 1/2009 |
| JP | 2009018173 A | 1/2009 |
| JP | 2011087733 A | 5/2011 |
| JP | 2012-526977 A | 11/2012 |
| JP | 2013007645 A | 1/2013 |
| JP | 2016528972 A | 9/2016 |
| KR | 10-1266966 B1 | 5/2013 |
| KR | 10-2016-041632 A | 4/2016 |
| KR | 10-2016-0071127 A | 6/2016 |
| WO | WO91/004713 A1 | 4/1991 |
| WO | WO94/010935 A1 | 5/1994 |
| WO | WO98/032394 A1 | 7/1998 |
| WO | WO98/044865 A1 | 10/1998 |
| WO | 2000/08415 A1 | 2/2000 |
| WO | WO2002/017776 A2 | 3/2002 |
| WO | WO2002/062252 A1 | 8/2002 |
| WO | WO02/095475 A1 | 11/2002 |
| WO | WO03/003932 A2 | 1/2003 |
| WO | WO2006/096558 A2 | 9/2006 |
| WO | WO2006/133548 A1 | 12/2006 |
| WO | WO2009/085752 A2 | 7/2009 |
| WO | WO2009/089129 A1 | 7/2009 |
| WO | WO2009/146788 A1 | 12/2009 |
| WO | WO2009/146789 A1 | 12/2009 |
| WO | WO2012/007003 A1 | 1/2012 |
| WO | WO2012/064684 A2 | 5/2012 |
| WO | WO2012/074304 A2 | 6/2012 |
| WO | WO2014/091865 A1 | 6/2014 |
| WO | 2015/015289 A2 | 2/2015 |
| WO | WO2015/015289 A2 | 2/2015 |
| WO | WO2015/063032 A1 | 5/2015 |
| WO | WO2015/176004 A1 | 11/2015 |
| WO | WO2016/004415 A1 | 1/2016 |
| WO | WO2016/042393 A1 | 3/2016 |
| WO | WO2016/061279 A1 | 4/2016 |
| WO | WO2016/084066 A1 | 6/2016 |
| WO | WO2016/099471 A1 | 6/2016 |
| WO | WO2016/113745 A1 | 7/2016 |
| WO | WO2016/116874 A1 | 7/2016 |
| WO | WO2018/085718 A2 | 5/2018 |

OTHER PUBLICATIONS

AADR. American Association for Dental Research; Summary of Activities; Los Angeles, CA; p. 195; Mar. 20-23,(year of pub. sufficiently earlier than effective US filed and any foreign priority date) 1980.

Alcaniz et al.; An Advanced System for the Simulation and Planning of Orthodontic Treatments; Karl Heinz Hohne and Ron Kikinis (eds.); Visualization in Biomedical Computing, 4th Intl. Conf, VBC '96, Hamburg, Germany; Springer-Verlag; pp. 511-520; Sep. 22-25, 1996.

Alexander et al.; The DigiGraph Work Station Part 2 Clinical Management; J. Clin. Orthod.; pp. 402-407; (Author Manuscript); Jul. 1990.

Allesee Orthodontic Appliance: Important Tip About Wearing the Red White & Blue Active Clear Retainer System; Allesee Orthodontic Appliances-Pro Lab; 1 page; (year of pub. sufficiently earlier than effective US filed and any foreign priority date); 1998.

Allesee Orthodontic Appliances: DuraClearTM; Porduct information; 1 page; (year of pub. sufficiently earlier than effective US filed and any foreign priority date) 1997.

Allesee Orthodontic Appliances; The Choice Is Clear: Red, White & Blue . . . The Simple, Affordable, No-Braces Treatment; ( product information for doctors); retrieved from the internet (http://ormco.com/aoa/appliancesservices/RWB/doctorhtml); 5 pages on May 19, 2003.

Allesee Orthodontic Appliances; The Choice Is Clear: Red, White & Blue . . . The Simple, Affordable, No-Braces Treatment; p(roduct information), 6 pages; (year of pub. sufficiently earlier than effective US filed and any foreign priority date) 2003.

Allesee Orthodontic Appliances; The Choice is Clear: Red, White & Blue . . . The Simple, Affordable, No-Braces Treatment;(Patient Information); retrieved from the internet (http://ormco.com/aoa/appliancesservices/RWB/patients.html); 2 pages on May 19, 2003.

Allesee Orthodontic Appliances; The Red, White & Blue Way to Improve Your Smile; (information for patients), 2 pages; (year of pub. sufficiently earlier than effective US filed and any foreign priority date) 1992.

Allesee Orthodontic Appliances; You may be a candidate for this invisible no-braces treatment; product information for patients; 2 pages; (year of pub. sufficiently earlier than effective US filed and any foreign priority date) 2002.

Altschuler et al.; Analysis of 3-D Data for Comparative 3-D Serial Growth Pattern Studies of Oral-Facial Structures; AADR Abstracts, Program and Abstracts of Papers, 57th General Session, IADR Annual Session, Mar. 29, 1979-Apr. 1, 1979, New Orleans Marriot; Journal of Dental Research; vol. 58, Special Issue A, p. 221; Jan. 1979.

Altschuler et al.; Laser Electro-Optic System for Rapid Three-Dimensional (3D) Topographic Mapping of Surfaces; Optical Engineering; 20(6); pp. 953-961; Dec. 1981.

Altschuler et al.; Measuring Surfaces Space-Coded by a Laser-Projected Dot Matrix; SPIE Imaging q Applications for Automated Industrial Inspection and Assembly; vol. 182; pp. 187-191; Oct. 10, 1979.

Altschuler; 3D Mapping of Maxillo-Facial Prosthesis; AADR Abstract #607; 2 pages total, (year of pub. sufficiently earlier than effective US filed and any foreign priority date) 1980.

Andersson et al.; Clinical Results with Titanium Crowns Fabricated with Machine Duplication and Spark Erosion; Acta Odontologica Scandinavica; 47(5); pp. 279-286; Oct. 1989.

Andrews, The Six Keys to Optimal Occlusion Straight Wire, Chapter 3, L.A. Wells; pp. 13-24; (year of pub. sufficiently earlier than effective US filed and any foreign priority date) 1989.

Barone et al.; Creation of 3D multi-body orthodontic models by using independent imaging sensors; Sensors; 13(2); pp. 2033-2050; Feb. 5, 2013.

Bartels et al.; An Introduction to Splines for Use in Computer Graphics and Geometric Modeling; Morgan Kaufmann Publishers; pp. 422-425 Jan. 1, 1987.

Baumrind et al, "Mapping the Skull in 3-D," reprinted from J. Calif. Dent. Assoc, 48(2), 11 pages; (year of pub. sufficiently earlier than effective US filed and any foreign priority date) Fall Issue 1972.

Baumrind et al.; A Stereophotogrammetric System for the Detection of Prosthesis Loosening in Total Hip Arthroplasty; NATO Symposium on Applications of Human Biostereometrics; SPIE; vol. 166; pp. 112-123; Jul. 9-13, 1978.

Baumrind; A System for Cranio facial Mapping Through the Integration of Data from Stereo X-Ray Films and Stereo Photographs;

(56) References Cited

OTHER PUBLICATIONS an invited paper submitted to the 1975 American Society of Photogram Symposium on Close-Range Photogram Systems; University of Illinois; pp. 142-166; Aug. 26-30, 1975.
Baumrind; Integrated Three-Dimensional Craniofacial Mapping: Background, Principles, and Perspectives; Seminars in Orthodontics; 7(4); pp. 223-232; Dec. 2001.
Bernard et al; Computerized Diagnosis in Orthodontics for Epidemiological Studies: A ProgressReport; (Abstract Only), J. Dental Res. Special Issue, vol. 67, p. 169, paper presented at International Association for Dental Research 66th General Session, Montreal Canada; Mar. 9-13, 1988,.
Bhatia et al.; A Computer-Aided Design for Orthognathic Surgery; British Journal of Oral and Maxillofacial Surgery; 22(4); pp. 237-253; Aug. 1, 1984.
Biggerstaff et al.; Computerized Analysis of Occlusion in the Postcanine Dentition; American Journal of Orthodontics; 61(3); pp. 245-254; Mar. 1972.
Biostar Operation & Training Manual. Great Lakes Orthodontics, Ltd. 199 Fire Tower Drive,Tonawanda, New York. 14150-5890, 20 pages; (year of pub. sufficiently earlier than effective US filed and any foreign priority date) 1990.
Bourke, Coordinate System Transformation; 1 page; retrived from the internet (http://astronomy.swin.edu.au/'pbourke/prolection/coords) on Nov. 5, 2004; Jun. 1996.
Boyd et al.; Three Dimensional Diagnosis and Orthodontic Treatment of Complex Malocclusions With the Invisalipn Appliance; Seminars in Orthodontics; 7(4); pp. 274-293; Dec. 2001.
Brandestini et al.; Computer Machined Ceramic Inlays: In Vitro Marginal Adaptation; J. Dent. Res. Special Issue; (Abstract 305); vol. 64; p. 208; (year of pub. sufficiently earlier than effective US filed and any foreign priority date) 1985.
Brook et al.; An Image Analysis System for the Determination of Tooth Dimensions from Study Casts: Comparison with Manual Measurements of Mesio-distal Diameter; Journal of Dental Research; 65(3); pp. 428-431; Mar. 1986.
Burstone et al.; Precision Adjustment of the Transpalatal Lingual Arch: Computer Arch Form Predetermination; American Journal of Orthodontics; 79(2);pp. 115-133; Feb. 1981.
Burstone; Dr. Charles J. Burstone on the Uses of the Computer in Orthodontic Practice (Part 1); Journal of Clinical Orthodontics; 13(7); pp. 442-453; (interview); Jul. 1979.
Burstone; Dr. Charles J. Burstone on The Uses of the Computer in Orthodontic Practice (Part 2); journal of Clinical Orthodontics; 13(8); pp. 539-551 (interview); Aug. 1979.
Cardinal Industrial Finishes; Powder Coatings; 6 pages; retrieved from the internet (http://www.cardinalpaint.com) on Aug. 25, 2000.
Carnaghan, An Alternative to Holograms for the Portrayal of Human Teeth; 4th Int'l. Conf. on Holographic Systems, Components and Applications; pp. 228-231; Sep. 15, 1993.
Chaconas et al,; The DigiGraph Work Station, Part 1, Basic Concepts; Journal of Clinical Orthodontics; 24(6); pp. 360-367; (Author Manuscript); Jun. 1990.
Chafetz et al.; Subsidence of the Femoral Prosthesis, A Stereophotogrammetric Evaluation; Clinical Orthopaedics and Related Research; No. 201; pp. 60-67; Dec. 1985.
Chiappone; Constructing the Gnathologic Setup and Positioner; Journal of Clinical Orthodontics; 14(2); pp. 121-133; Feb. 1980.
Chishti et al.; U.S. Appl. No. 60/050,342 entitled "Procedure for moving teeth using a seires of retainers," filed Jun. 20, 1997.
Cottingham; Gnathologic Clear Plastic Positioner; American Journal of Orthodontics; 55(1); pp. 23-31; Jan. 1969.
Crawford; CAD/CAM in the Dental Office: Does It Work?; Canadian Dental Journal; 57(2); pp. 121-123 Feb. 1991.
Crawford; Computers in Dentistry: Part 1: CAD/CAM: The Computer Moves Chairside, Part 2: F. Duret ' A Man With A Vision, Part 3: The Computer Gives New Vision—Literally, Part 4: Bytes 'N Bites The Computer Moves From The Front Desk to The Operatory; Canadian Dental Journal; 54(9); pp. 661-666 Sep. 1988.
Crooks; CAD/CAM Comes to USC; USC Dentistry; pp. 14-17; (year of pub. sufficiently earlier than effective US filed and any foreign priority date) Spring 1990.
Cureton; Correcting Malaligned Mandibular Incisors with Removable Retainers; Journal of Clinical Orthodontics; 30(7); pp. 390-395; Jul. 1996.
Curry et al.; Integrated Three-Dimensional Craniofacial Mapping at the Craniofacial Research InstrumentationLaboratory/University of the Pacific; Seminars in Orthodontics; 7(4); pp. 258-265; Dec. 2001.
Cutting et al.; Three-Dimensional Computer-Assisted Design of Craniofacial Surgical Procedures: Optimization and Interaction with Cephalometric and CT-Based Models; Plastic and Reconstructive Surgery; 77(6); pp. 877-885; Jun. 1986.
DCS Dental AG; The CAD/CAM 'DCS Titan System' for Production of Crowns/Bridges; DSC Production; pp. 1-7; Jan. 1992.
Defranco et al.; Three-Dimensional Large Displacement Analysis of Orthodontic Appliances; Journal of Biomechanics; 9(12); pp. 793-801; Jan. 1976.
Dental Institute University of Zurich Switzerland; Program for International Symposium on Computer Restorations: State of the Art of the CEREC-Method; 2 pages; May 1991.
Dentrac Corporation; Dentrac document; pp. 4-13; (year of pub. sufficiently earlier than effective US filed and any foreign priority date) 1992.
Dent-x; Dentsim . . . Dent-x's virtual reality 3-D training simulator . . . A revolution in dental education; 6 pages; retrieved from the Internet (http://www.dent-x.com/DentSim.htm); on Sep. 24, 1998.
Doyle; Digital Dentistry; Computer Graphics World; pp. 50-52 andp. 54; Oct. 2000.
Duret et al.; CAD/CAM Imaging in Dentistry; Current Opinion in Dentistry; 1(2); pp. 150-154; Apr. 1991.
Duret et al; CAD-CAM in Dentistry; Journal of the American Dental 117(6); pp. 715-720; Nov. 1988.
Duret; The Dental CAD/CAM, General Description of the Project; Hennson International Product Brochure, 18 pages; Jan. 1986.
Duret; Vers Une Prosthese Informatisee; Tonus; 75(15); pp. 55-57; (English translation attached); Nov. 15, 1985.
Economides; The Microcomputer in the Orthodontic Office; Journal of Clinical Orthodontics; 13(11); pp. 767-772; Nov. 1979.
Elsasser; Some Observations on the History and Uses of the Kesling Positioner; American Journal of Orthodontics; 36(5); pp. 368-374; May 1, 1950.
English translation of Japanese Laid-Open Publication No. 63-11148 to inventor T. Ozukuri (Laid-Open on Jan. 18, 1998) pp. 1-7.
Faber et al.; Computerized Interactive Orthodontic Treatment Planning; American Journal of Orthodontics; 73(1); pp. 36-46; Jan. 1978.
Felton et al.; A Computerized Analysis of the Shape and Stability of Mandibular Arch Form; American Journal of Orthodontics and Dentofacial Orthopedics; 92(6); pp. 478-483; Dec. 1987.
Friede et al.; Accuracy of Cephalometric Prediction in Orthognathic Surgery; Journal of Oral and Maxillofacial Surgery; 45(9); pp. 754-760; Sep. 1987.
Futterling et al.; Automated Finite Element Modeling of a Human Mandible with Dental Implants; JS WSCG '98—Conference Program; 8 pages; retrieved from the Internet (https://dspace5.zcu.cz/bitstream/11025/15851/1/Strasser_98.pdf); on Aug. 21, 2018.
Gim-Alldent Deutschland, "Das DUX System: Die Technik," 3 pages; (English Translation Included); (year of pub. sufficiently earlier than effective US filed and any foreign priority date); 2002.
Gottleib et al.; JCO Interviews Dr. James A. McNamura, Jr., on the Frankel Appliance: Part 2: Clinical 1-1 Management; Journal of Clinical Orthodontics; 16(6); pp. 390-407; retrieved from the internet (http://www.jco-online.com/archive/print_article.asp?Year=1982&Month=06&ArticleNum+); 21 pages; Jun. 1982.
Grayson; New Methods for Three Dimensional Analysis of Craniofacial Deformity, Symposium: Computerized Facial Imaging in Oral and Maxillofacial Surgery; American Association of Oral and Maxillofacial Surgeons; 48(8) suppl 1; pp. 5-6; Sep. 13, 1990.
Guess et al.; Computer Treatment Estimates in Orthodontics and Orthognathic Surgery; Journal of Clinical Orthodontics; 23(4); pp. 262- 268; 11 pages; (Author Manuscript); Apr. 1989.

(56) References Cited

OTHER PUBLICATIONS

Heaven et al.; Computer-Based Image Analysis of Artificial Root Surface Caries; Abstracts of Papers #2094; Journal of Dental Research; 70:528; (Abstract Only); Apr. 17-21, 1991.
Highbeam Research; Simulating stress put on jaw. (ANSYS Inc.'s finite element analysis software); 2 pages; retrieved from the Internet (http://static.highbeam.eom/t/toolingampproduction/november011996/simulatingstressputonfa..); on Nov. 5, 2004.
Hikage; Integrated Orthodontic Management System for Virtual Three-Dimensional Computer Graphic Simulation and Optical Video Image Database for Diagnosis and Treatment Planning; Journal of Japan KA Orthodontic Society; 46(2); pp. 248-269; 56 pages; (English Translation Inclused); Feb. 1987.
Hoffmann et al.; Role of Cephalometry for Planning of Jaw Orthopedics and Jaw Surgery Procedures; Informatbnen, pp. 375-396; (English Abstract Included); Mar. 1991.
Hojjatie et al.; Three-Dimensional Finite Element Analysis of Glass-Ceramic Dental Crowns; Journal of Biomechanics; 23(11); pp. 1157-1166; Jan. 1990.
Huckins; CAD-CAM Generated Mandibular Model Prototype from MRI Data; AAOMS, p. 96; (Abstract Only); (year of pub. sufficiently earlier than effective US filed and any foreign priority date) 1999.
JCO Interviews; Craig Andreiko , DDS, MS on the Elan and Orthos Systems; Interview by Dr. Larry W. White; Journal of Clinical Orthodontics; 28(8); pp. 459-468; 14 pages; (Author Manuscript); Aug. 1994.
JCO Interviews; Dr. Homer W. Phillips on Computers in Orthodontic Practice, Part 2; Journal of Clinical Orthodontics; 17(12); pp. 819-831; 19 pages; (Author Manuscript); Dec. 1983.
Jerrold; The Problem, Electronic Data Transmission and the Law; American Journal of Orthodontics and Dentofacial Orthopedics; 113(4); pp. 478-479; 5 pages; (Author Manuscript); Apr. 1998.
Jones et al.; An Assessment of the Fit of a Parabolic Curve to Pre- and Post-Treatment Dental Arches; British Journal of Orthodontics; 16(2); pp. 85-93; May 1989.
Kesling et al.; The Philosophy of the Tooth Positioning Appliance; American Journal of Orthodontics and Oral surgery; 31(6); pp. 297-304; Jun. 1945.
Kesling; Coordinating the Predetermined Pattern and Tooth Positioner with Conventional Treatment; American Journal of Orthodontics and Oral Surgery; 32(5); pp. 285-293; May 1946.
Kleeman et al.; The Speed Positioner; J. Clin. Orthod.; 30(12); pp. 673-680; Dec. 1996.
Kuroda et al.; Three-Dimensional Dental Cast Analyzing System Using Laser Scanning; American Journal of Orthodontics and Dentofacial Orthopedics; 110(4); pp. 365-369; Oct. 1996.
Laurendeau et al.; A Computer-Vision Technique for the Acquisition and Processing of 3-D Profiles of 7 Dental Imprints: An Application in Orthodontics; IEEE Transactions on Medical Imaging; 10(3); pp. 453-461; Sep. 1991.
Leinfelder et al.; A New Method for Generating Ceramic Restorations: a CAD-CAM System; Journal of the American Dental Association; 118(6); pp. 703-707; Jun. 1989.
Manetti et al.; Computer-Aided Cefalometry and New Mechanics in Orthodontics; Fortschr Kieferorthop; 44; pp. 370-376; 8 pages; (English Article Summary Included); (year of pub. sufficiently earlier than effective US filed and any foreign priority date) 1983.
McCann; Inside the ADA; J. Amer. Dent. Assoc, 118:286-294; Mar. 1989.
McNamara et al.; Invisible Retainers; J. Clin Orthod.; pp. 570-578; 11 pages; (Author Manuscript); Aug. 1985.
McNamara et al.; Orthodontic and Orthopedic Treatment in the Mixed Dentition; Needham Press; pp. 347-353; Jan. 1993.
Moermann et al, Computer Machined Adhesive Porcelain Inlays: Margin Adaptation after Fatigue Stress; IADR Abstract 339; J. Dent. Res.; 66(a);763; (Abstract Only); (year of pub. sufficiently earlier than effective US filed and any foreign priority date) 1987.
Moles; Correcting Mild Malalignments—As Easy As One, Two, Three; AOA/Pro Corner; 11(2); 2 pages; (year of pub. sufficiently earlier than effective US filed and any foreign priority date) 2002.
Mormann et al.; Marginale Adaptation von adhasuven Porzellaninlays in vitro; Separatdruck aus:Schweiz. Mschr. Zahnmed.; 95; pp. 1118-1129; 8 pages; (Macine Translated English Abstract); (year of pub. sufficiently earlier than effective US filed and any foreign priority date); 1985.
Nahoum; The Vacuum Formed Dental Contour Appliance; N. Y. State Dent. J.; 30(9); pp. 385-390; Nov. 1964.
Nash; CEREC CAD/CAM Inlays: Aesthetics and Durability in a Single Appointment; Dentistry Today; 9(8); pp. 20, 22-23 and 54; Oct. 1990.
Ogawa et al.; Mapping, profiling and clustering of pressure pain threshold (PPT) in edentulous oral muscosa; Journal of Dentistry; 32(3); pp. 219-228; Mar. 2004.
Ogimoto et al.; Pressure-pain threshold determination in the oral mucosa; Journal of Oral Rehabilitation; 29(7); pp. 620-626; Jul. 2002.
Paul et al.; Digital Documentation of Individual Human Jaw and Tooth Forms for Applications in Orthodontics; Oral Surgery and Forensic Medicine Proc. of the 24th Annual Conf. of the IEEE Industrial Electronics Society (IECON '98); vol. 4, pp. 2415-2418; Sep. 4, 1998.
Pinkham; Foolish Concept Propels Technology; Dentist, 3 pages , Jan./Feb. 1989.
Pinkham; Inventor's CAD/CAM May Transform Dentistry; Dentist; pp. 1 and 35, Sep. 1990.
Ponitz; Invisible retainers; Am. J. Orthod.; 59(3); pp. 266-272; Mar. 1971.
Procera Research Projects; Procera Research Projects 1993 ' Abstract Collection; 23 pages; (year of pub. sufficiently earlier than effective US filed and any foreign priority date) 1993.
Proffit et al.; the first stage of comprehensive treatment alignment and leveling; Contemporary Orthodontics, 3rd Ed.; Chapter 16; Mosby Inc.; pp. 534-537; (year of pub. sufficiently earlier than effective US filed and any foreign priority date) 2000.
Proffit et al.; The first stage of comprehensive treatment: alignment and leveling; Contemporary Orthodontics; (Second Ed.); Chapter 15, MosbyYear Book; St. Louis, Missouri; pp. 470-533 Oct. 1993.
Raintree Essix & ARS Materials, Inc., Raintree Essix, Technical Magazine Table of contents and Essix Appliances, 7 pages; retrieved from the internet (http://www.essix.com/magazine/defaulthtml) on Aug. 13, 1997.
Redmond et al.; Clinical Implications of Digital Orthodontics; American Journal of Orthodontics and Dentofacial Orthopedics; 117(2); pp. 240-242; Feb. 2000.
Rekow et al.; CAD/CAM for Dental Restorations—Some of the Curious Challenges; IEEE Transactions on Biomedical Engineering; 38(4); pp. 314-318; Apr. 1991.
Rekow et al.; Comparison of Three Data Acquisition Techniques for 3-D Tooth Surface Mapping; Annual International Conference of the IEEE Engineering in Medicine and Biology Society; 13(1); pp. 344-345 (year of pub. sufficiently earlier than effective US filed and any foreign priority date) 1991.
Rekow; A Review of the Developments in Dental CAD/CAM Systems; Current Opinion in Dentistry; 2; pp. 25-33; Jun. 1992.
Rekow; CAD/CAM in Dentistry: A Historical Perspective and View of the Future; Journal Canadian Dental Association; 58(4); pp. 283, 287-288; Apr. 1992.
Rekow; Computer-Aided Design and Manufacturing in Dentistry: A Review of the State of the Art; Journal of Prosthetic Dentistry; 58(4); pp. 512-516; Dec. 1987.
Rekow; Dental CAD-CAM Systems: What is the State of the Art?; The Journal of the American Dental Association; 122(12); pp. 43-48; Dec. 1991.
Rekow; Feasibility of an Automated System for Production of Dental Restorations, Ph.D. Thesis; Univ. of Minnesota, 250 pages, Nov. 1988.
Richmond et al.; The Development of a 3D Cast Analysis System; British Journal of Orthodontics; 13(1); pp. 53-54; Jan. 1986.

(56) References Cited

OTHER PUBLICATIONS

Richmond; Recording The Dental Cast in Three Dimensions; American Journal of Orthodontics and Dentofacial Orthopedics; 92(3); pp. 199-206; Sep. 1987.
Rudge; Dental Arch Analysis: Arch Form, A Review of the Literature; The European Journal of Orthodontics; 3(4); pp. 279-284; Jan. 1981.
Sakuda et al.; Integrated Information-Processing System in Clinical Orthodontics: An Approach with Use of a Computer Network System; American Journal of Orthodontics and Dentofacial Orthopedics; 101(3); pp. 210-220; 20 pages; (Author Manuscript) Mar. 1992.
Schellhas et al.; Three-Dimensional Computed Tomography in Maxillofacial Surgical Planning; Archives of Otolaryngology—Head and Neck Surgery; 114(4); pp. 438-442; Apr. 1988.
Schroeder et al; Eds. The Visual Toolkit, Prentice Hall PTR, New Jersey; Chapters 6, 8 & 9, (pp. 153-210,309-354, and 355-428; (year of pub. sufficiently earlier than effective US filed and any foreign priority date) 1998.
Shilliday; Minimizing finishing problems with the mini-positioner; American Journal of Orthodontics; 59(6); pp. 596-599; Jun. 1971.
Shimada et al.; Application of optical coherence tomography (OCT) for diagnosis of caries, cracks, and defects of restorations; Current Oral Health Reports; 2(2); pp. 73-80; Jun. 2015.
Siemens; CEREC—Computer-Reconstruction, High Tech in der Zahnmedizin; 15 pagesl; (Includes Machine Translation); (year of pub. sufficiently earlier than effective US filed and any foreign priority date); 2004.
Sinclair; The Readers' Corner; Journal of Clinical Orthodontics; 26(6); pp. 369-372; 5 pages; retrived from the internet (http://www.jco-online.com/archive/print_article.asp?Year=1992&Month=06&ArticleNum=); Jun. 1992.
Stoll et al.; Computer-aided Technologies in Dentistry; Dtsch Zahna'rztl Z 45, pp. 314-322; (English Abstract Included); (year of pub. sufficiently earlier than effective US filed and any foreign priority date) 1990.
The American Heritage, Stedman's Medical Dictionary; Gingiva; 3 pages; retrieved from the interent (http://reference.com/search/search?q=gingiva) on Nov. 5, 2004.
The Dental Company Sirona: Cerc omnicam and cerec bluecam brochure: The first choice in every case; 8 pages; (year of pub. sufficiently earlier than effective US filed and any foreign priority date) 2014.
Thorlabs; Pellin broca prisms; 1 page; retrieved from the internet (www.thorlabs.com); Nov. 30, 2012.
Tiziani et al.; Confocal principle for macro and microscopic surface and defect analysis; Optical Engineering; 39(1); pp. 32-39; Jan. 1, 2000.
Truax; Truax Clasp-Less(TM) Appliance System; The Functional Orthodontist; 9(5); pp. 22-24, 26-8; Sep.-Oct. 1992.
Tru-Tatn Orthodontic & Dental Supplies, Product Brochure, Rochester, Minnesota 55902, 16 pages; (year of pub. sufficiently earlier than effective US filed and any foreign priority date) 1996.
U.S. Department of Commerce, National Technical Information Service, Holodontography: An Introduction to Dental Laser Holography; School of Aerospace Medicine Brooks AFB Tex; Mar. 1973, 40 pages; Mar. 1973.
U.S. Department of Commerce, National Technical Information Service; Automated Crown Replication Using Solid Photography SM; Solid Photography Inc., Melville NY,; 20 pages; Oct. 1977.
Van Der Linden et al.; Three-Dimensional Analysis of Dental Casts by Means of the Optocom; Journal of Dental Research; 51(4); p. 1100; Jul.-Aug. 1972.
Van Hilsen et al.; Comparing potential early caries assessment methods for teledentistry; BMC Oral Health; 13(16); doi: 10.1186/1472-6831-13-16; 9 pages; Mar. 2013.
Varady et al.; Reverse Engineering of Geometric Models'An Introduction; Computer-Aided Design; 29(4); pp. 255-268; 20 pages; (Author Manuscript); Apr. 1997.
Warunek et al.; Physical and Mechanical Properties of Elastomers in Orthodonic Positioners; American Journal of Orthodontics and Dentofacial Orthopedics; 95(5); pp. 388-400; 21 pages; (Author Manuscript); May 1989.
Warunek et.al.; Clinical Use of Silicone Elastomer Applicances; JCO; 23 (10); pp. 694-700; Oct. 1989.
Wells; Application of the Positioner Appliance in Orthodontic Treatment; American Journal of Orthodontics; 58(4); pp. 351-366; Oct. 1970.
Williams; The Switzerland and Minnesota Developments in CAD/CAM; Journal of Dental Practice Administration; 4(2); pp. 50-55; Apr./Jun. 1987.
Wishan; New Advances in Personal Computer Applications for Cephalometric Analysis, Growth Prediction, Surgical Treatment Planning and Imaging Processing; Symposium: Computerized Facial Imaging in Oral and Maxilofacial Surgery; p. 5; Presented on Sep. 13, 1990.
WSCG'98—Conference Program, The Sixth International Conference in Central Europe on Computer Graphics and Visualization '98; pp. 1-7; retrieved from the Internet on Nov. 5, 2004, (http://wscg.zcu.cz/wscg98/wscg98.htm); Feb. 9-13, 1998.
Yamamoto et al.; Optical Measurement of Dental Cast Profile and Application to Analysis of Three-Dimensional Tooth Movement in Orthodontics; Front. Med. Biol. Eng., 1(2); pp. 119-130; (year of pub. sufficiently earlier than effective US filed and any foreign priority date); 1988.
Yamamoto et al.; Three-Dimensional Measurement of Dental Cast Profiles and Its Applications to Orthodontics; Conf. Proc. IEEE Eng. Med. Biol. Soc.; 12(5); pp. 2052-2053; Nov. 1990.
Yoshii; Research on a New Orthodontic Appliance: The Dynamic Positioner (D.P.); 111. The General Concept of the D.P. Method and Its Therapeutic Effect, Part 1, Dental and Functional Reversed Occlusion Case Reports; Nippon Dental Review; 457; pp. 146-164; 43 pages; (Author Manuscript); Nov. 1980.
Yoshii; Research on a New Orthodontic Appliance: The Dynamic Positioner (D.P.); I. The D.P. Concept and Implementation of Transparent Silicone Resin (Orthocon); Nippon Dental Review; 452; pp. 61-74; 32 pages; (Author Manuscript); Jun. 1980.
Yoshii; Research on a New Orthodontic Appliance: The Dynamic Positioner (D.P.); II. The D.P. Manufacturing Procedure and Clinical Applications; Nippon Dental Review; 454; pp. 107-130; 48 pages; (Author Manuscript); Aug. 1980.
Yoshii; Research on a New Orthodontic Appliance: The Dynamic Positioner (D.P.); III—The General Concept of the D.P. Method and Its Therapeutic Effect, Part 2. Skeletal Reversed Occlusion Case Reports; Nippon Dental Review; 458; pp. 112-129; 40 pages; (Author Manuscript); Dec. 1980.
Canadian Intellectual Property Office, Office Action for Canadian Patent Application No. 2,949,448 dated Sep. 26, 2017, 3 pages.
International Preliminary Report on Patentability and Written Opinion for International Application No. PCT/IB2015/054950 dated Jan. 10, 2017, 12 pages.
International Search Report and Written Opinion for International Patent Application No. PCT/US2018/013321 dated Apr. 26, 2018, 16 pages.
International Search Report and Written Opinion for PCT Application No. PCT/IB2015/001400 dated Feb. 9, 2016, 18 pages.
International Search Report and Written Opinion for PCT Application No. PCT/IB2015/054950 dated Apr. 1, 2016, 19 pages.
IP Australia, Examination Report No. 1 for Patent Application No. 2015287312 dated Jul. 31, 2017, 5 pages.
IP Australia, Examination Report No. 2 for Patent Application No. 2015287312 dated Feb. 12, 2018, 4 pages.
Japanese Patent Office, Office Action for Japanese Patent Application No. JP 2017-500896 dated Dec. 18, 2018, 4 pages.
Japanese Patent Office, Office Action for Japanese Patent Application No. JP 2017-500896, with English translation, dated May 29, 2018, 15 pages.
Korean Intellectual Property Office, Notification of Reason for Refusal for Korean Patent Application No. 10-2017-7003299 dated Nov. 14, 2017, including English translation, 15 pages.

(56) References Cited

OTHER PUBLICATIONS

Doruk et al.; The role of the headgear timer in extraoral co-operation; European Journal of Orthodontics; 26; pp. 289-291; Jun. 1, 2004.
Friedrich et al; Measuring system for in vivo recording of force systems in orthodontic treatment-concept and analysis of accuracy; J. Biomech.; 32(1); pp. 81-85; (Abstract Only) Jan. 1999.
Grest, Daniel; Marker-Free Human Motion Capture in Dynamic Cluttered Environments from a Single View-Point, PhD Thesis; 171 pages; Dec. 2007.
Invisalign; You were made to move. There's never been a better time to straighten your teeth with the most advanced clear aligner in the world; Product webpage; 2 pages; retrieved from the internet (www.invisalign.com/) on Dec. 28, 2017.
Kumar et al.; Rapid maxillary expansion: A unique treatment modality in dentistry; J. Clin. Diagn. Res.; 5(4); pp. 906-911; Aug. 2011.
Nedelcu et al.; "Scanning Accuracy and Precision in 4 Intraoral Scanners: an In Vitro Comparison Based on 3-Dimensional Analysis"; J. Prosthet. Dent.; 112(6); pp. 1461-71; Dec. 2014.
Sahm et al.; "Micro-Electronic Monitoring of Functional Appliance Wear"; Eur J Orthod.; 12(3); pp. 297-301; Aug. 1990.
Sahm; Presentation of a wear timer for the clarification of scientific questions in orthodontic orthopedics; Fortschritte der Kieferorthopadie; 51 (4); pp. 243-247; (Translation Included) Jul. 19990.
Schafer et al.; "Quantifying patient adherence during active orthodontic treatment with removable appliances using microelectronic wear-time documentation"; Eur J Orthod.; 37(1)pp. 1-8; doi:10.1093/ejo/cju012; Jul. 3, 2014.
Thera Mon; "Microsensor"; "2 pages"; retrieved from the interent (www.english.thera-mon.com/the-product/transponder/index.html); on Sep. 19, 2016.
Wikipedia; Palatal expansion; 3 pages; retrieved from the internet (https://en.wikipedia.org/wiki/Palatal_expansion) on Mar. 5, 2018.
Wireless Sensor Networks Magazine; Embedded Teeth for Oral Activity Recognition; 2 pages; retrievedon Sep. 19, 2016 from the internet (www.wsnmagazine.com/embedded-teeth/); Jul. 29, 2013.
Witt et al.; The wear-timing measuring device in orthodontics-cui Bono? Reflections on the state-of-the-art in wear-timing measurement and compliance research in orthodontics; Fortschr Kieferorthop.; 52(3); pp. 117-125; (Translation Included) Jun. 1991.
Yamada et al.; Simulation of fan-beam type optical computed-tomography imaging of strongly scattering and weakly absorbing media; Applied Optics; 32(25); pp. 4808-4814; Sep. 1, 1993.
Carrier et al.; U.S. Appl. No. 15/803,718 entitled "Methods and apparatuses for dental images," filed Nov. 3, 2017.
Kuo; U.S. Appl. No. 15/829,504 entitled "Dental appliance features for speech enhancement," filed Dec. 1, 2017.
Shanjani et al.; U.S. Appl. No. 15/831,159 entitled "Palatal expanders and methods of expanding a palate," filed Dec. 4, 2017.
Wu et al.; U.S. Appl. No. 15/831,262 entitled "Methods and apparatuses for customizing a rapid palatal expander," filed Dec. 4, 2017.
Grove et al.; U.S. Appl. No. 15/726,243 entitled "Interproximal reduction templates," filed Oct. 5, 2017.
Begole et al.; A Computer System for the Analysis of Dental Casts; The Angle Orthodontist; 51(3); pp. 252-258; Jul. 1981.
Biggerstaff; Computerized Diagnostic Setups and Simulations; Angle Orthodontist; 40(I); pp. 28-36; Jan. 1970.
Blu et al.; Linear interpolation revitalized; IEEE Transactions on Image Processing; 13(5); pp. 710-719; May 2004.
Dummer et al.; Computed Radiography Imaging Based on High-Density 670 nm VCSEL Arrays; International Society for Optics and Photonics; vol. 7557; p. 75570H; 7 pages; (Author Manuscript); Feb. 24, 2010.

Gao et al.; 3-D element Generation for Multi-Connected Complex Dental and Mandibular Structure; IEEE Proceedings International Workshop in Medical Imaging and Augmented reality; pp. 267-271; Jun. 12, 2001.
Kamada et.al.; Case Reports on Tooth Positioners Using LTV Vinyl Silicone Rubber; J. Nihon University School of Dentistry; 26(1); pp. 11-29; (year of pub. sufficiently earlier than effective US filed and any foreign priority date) 1984.
Kamada et.al.; Construction of Tooth Positioners with LTV Vinyl Silicone Rubber and Some Case KJ Reports; J. Nihon University School of Dentistry; 24(1); pp. 1-27; (year of pub. sufficiently earlier than effective US filed and any foreign priority date) 1982.
Kanazawa et al.; Three-Dimensional Measurements of the Occlusal Surfaces of Upper Molars in a Dutch Population; Journal of Dental Research; 63(11); pp. 1298-1301; Nov. 1984.
Kochanek; Interpolating Splines with Local Tension, Continuity and Bias Control; Computer Graphics; 18(3); pp. 33-41; Jan. 1, 1984.
Kunii et al.; Articulation Simulation for an Intelligent Dental Care System; Displays; 15(3); pp. 181-188; Jul. 1994.
Nishiyama et al.; A New Construction of Tooth Repositioner by LTV Vinyl Silicone Rubber; The Journal of Nihon University School of Dentistry; 19(2); pp. 93-102 (year of pub. sufficiently earlier than effective US filed and any foreign priority date) 1977.
Richmond et al.; The Development of the PAR Index (Peer Assessment Rating): Reliability and Validity.; The European Journal of Orthodontics; 14(2); pp. 125-139; Apr. 1992.
Sturman; Interactive Keyframe Animation of 3-D Articulated Models; Proceedings Graphics Interface '84; vol. 86; pp. 35-40; May-Jun. 1984.
Van Der Linden; A New Method to Determine Tooth Positions and Dental Arch Dimensions; Journal of Dental Research; 51(4); p. 1104; Jul.-Aug. 1972.
Van Der Zel; Ceramic-Fused-to-Metal Restorations with a New CAD/CAM System; Quintessence International; 24(A); pp. 769-778; (year of pub. sufficiently earlier than effective US filed and any foreign priority date); 1993.
Verstreken et al.; An Image-Guided Planning System for Endosseous Oral Implants; IEEE Transactions on Medical Imaging; 17(5); pp. 842-852; Oct. 1998.
Williams; Dentistry and CAD/CAM: Another French Revolution; J. Dent. Practice Admin.; 4(1); pp. 2-5 Jan./Mar. 1987.
Xia et al.; Three-Dimensional Virtual-Reality Surgical Planning and Soft-Tissue Prediction for Orthognathic Surgery; IEEE Transactions on Information Technology in Biomedicine; 5(2); pp. 97-107; Jun. 2001.
Yamany et al.; A System for Human Jaw Modeling Using Intra-Oral Images; Proc. of the 20th Annual Conf. of the IEEE Engineering in Medicine and Biology Society; vol. 2; pp. 563-566; Oct. 1998,.
Cramer; U.S. Appl. 15/937,569 entitled "Apparatuses and methods assisting in dental therapies," filed Mar. 27, 2018.
Cramer et al.; U.S. Appl. No. 15/942,341 entitled "Orthodontic appliances including at least partially un-erupted teeth and method of forming them," filed Mar. 30, 2018.
Office Action for Chinese Patent Application No. 201580037043.X dated Jan. 2, 2019, with English translation, 18 pages.
Office Action for Chinese Patent Application No. 201580056255.2 dated Jan. 16, 2019,Chinese only, 7 pages.
Second Office Action for Chinese Patent Application No. 201580037043.X dated Jun. 19, 2019, with English translation, 22 pages.
Japanese Patent Office, Office Action for Japanese Patent Application No. JP 2017-500896 dated Jun. 11, 2019, with English translation, 6 pages.
Park Hong-Seok et al., "Development of High Speed and High Accuracy 3D Dental Intra Oral Scanner," Procedia Eng. 100 (2015) 1174-1181.†

† cited by third party

COMPACT CONFOCAL DENTAL SCANNING APPARATUS

CROSS REFERENCE TO RELATED APPLICATIONS

This patent application claims priority to U.S. provisional patent application No. 62/445,663, filed Jan. 12, 2017, and titled "COMPACT CONFOCAL DENTAL SCANNING APPARATUS," which is herein incorporated by reference in its entirety.

The following U.S. patent applications are herein incorporated by reference in their entirety to the same extent as if each individual publication or patent application was specifically and individually indicated to be incorporated by reference: U.S. patent application Ser. No. 14/741,172, titled "APPARATUS FOR DENTAL CONFOCAL IMAGING," filed on Jun. 16, 2015, and U.S. patent application Ser. No. 14/825,173, titled "CONFOCAL IMAGING APPARATUS WITH CURVED FOCAL SURFACE," filed on Aug. 13, 2015.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This disclosure relates generally to apparatuses and methods for three dimensional (3D) scanning of objects. In particular, the disclosure relates to apparatuses and methods for three dimensional (3D) scanning of teeth in a patient's mouth.

BACKGROUND

Three dimensional scanning of an object is valuable in many clinical applications. For example, in the fields of orthodontics and prosthodontics, three dimensional (3D) scanning of the teeth can provide valuable information for diagnosis and treatment such as dental restorative and orthodontics indications. Confocal 3D scanning is one of the imaging technologies that may provide such information. Confocal microscopy may be used to perform three dimensional scanning by illuminating and observing a single nearly diffraction limited spot, for example, by using a spatial pinhole to eliminate out-of-focus light. Confocal 3D scanning can be used to obtain images free of defocus-blur and may allow three-dimensional visualization of the object. Other surface topology scanners have been described, but are generally relatively bulky and may be less comfortable or may even be difficult to use. U.S. Pat. No. 8,878,905 describes a 3D scanner for obtaining the 3D geometry of an object using confocal pattern projection techniques. The 3D scanner disclosed therein uses a time varying pattern (or a segmented light source to equivalently create a time varying pattern). When the pattern is varied in time for a fixed focus plane then the in-focus regions on the object will display an oscillating pattern of light and darkness. However, the out-of-focus regions will display smaller or no contrast in the light oscillations.

Thus, there is a need for develop apparatuses and related methods for confocal scanning to have a more compact size, lighter weight and lower cost than the conventional confocal scanning apparatuses.

SUMMARY OF THE DISCLOSURE

Described herein are apparatuses and methods for confocal 3D scanning of an object, for example, at least apportion of teeth in a patient's mouth.

For example, described herein are apparatuses for confocal 3D scanning of a subject's dentation. The apparatus can comprise a confocal illuminator configured to generate confocal illumination to an object. The confocal illuminator can comprise a spatial pattern disposed on a transparent base and a light source configured to provide illumination to the spatial pattern. The apparatus can comprise an optical system comprising one or more lenses and having an optical axis. The apparatus can comprise a depth scanning module configured to be movable along the optical axis. The apparatus can further comprise a beam splitter configured to transmit light beams of the confocal illuminator to the object and reflect light beams returned from the object. The apparatus can comprise an image sensor configured to receive light beams returned from the object through the beam splitter. The apparatus can be configured for 3D scanning to at least a portion of the object, for example, intraoral dental 3D scanning for all derivatives of dental restorative and orthodontics indications.

In general, the apparatus for confocal scanning disclosed herein can comprise a confocal illuminator, for example, an LED illuminated transparency confocal illuminator. In general, the apparatus can comprise an optical system (including projection/imaging optics) configured to illuminate the object and image the object. The optical system can comprise a projection and imaging system or subsystem and an illumination subsystem (illumination optics). For example, the projection/imaging optics system may include optical elements (lenses) and the same optical path. The apparatus can comprise a depth scanning module, which may comprise a compact linear actuator, for example, a voice coil motor (VCM). The apparatus can comprise a front tip, which can include a 45 degree back heated mirror.

For example, the portion of the optical system between the beam splitter and the front tip can be configured small enough to be disposed entirely into the depth scanning module. Therefore, the apparatus confocal scanning can comprise a single opto-mechanical module for imaging and depth scanning. The single optomechanical module integrating the optical system and the depth scanning module can leads to relaxed production and assembly tolerances as well as reduced manufacturing cost. The optical design is suitable for LED illuminated transparency, which further enables low cost manufacturing. The optical system can further comprise reduced number of lenses, for example, the optical system can comprise less than 10 lenses, less than 9 lenses, less than 5 lenses, less than 3 lenses, etc. The optical system (e.g., protection/imaging optics system) in any of the apparatuses described herein may provide an axial magnification of between 5 and 20 (e.g., 11×). Furthermore, the optical system disclosed herein may be less sensitive to assembly errors and thermal variations than conventional confocal optical systems because of simpler configuration. The apparatus can comprise the optical system configured for maximum deviation from telecentricity towards divergent chief rays, for minimal front tip size. The apparatus can have a non-telecentric configuration in object space, for example, diverging confocal beams in object space.

In general, the apparatus can further comprise a polarized beam splitter for confocal junction. The apparatus can be configured for drift invariant confocal conjugation. The apparatus can further support monolithic confocal conjugate assembly. In general, the confocal scanning apparatus can be compact, light weighted, and low cost. For example, the apparatus can be more compact (e.g., 2×, 3×, or 4×) and lighter (e.g., 2× or 3×) than a typical conventional confocal scanners having the same scanning capability. The apparatus can further comprise a compact high speed image sensor. For example, the apparatus can be compact and light weighted to be handheld. The scan speed can be about 5, 10, 20, 50 scans/sec or any values therebetween. For example, the scan speed can be about 10 scans/sec.

The spatial pattern on the transparent base may be static (e.g., not time varying). The transparent base may comprise a transparency. The beam splitter may comprise a polarization sensitive beam splitter, wherein the spatial pattern and the transparent base are bonded onto a first side of the beam splitter, wherein the image sensor is bonded to a second side of the beam splitter perpendicular to the first side to maintain stable relative position between the image sensor and the spatial pattern.

For example, the confocal illuminator may be configured such that an image of the light source is positioned at an entrance pupil of the optical system. The spatial pattern may be disposed at a conjugate plane of the image sensor such that a position of an image of the object is invariant to relative lateral shift of the spatial pattern to the image sensor. An exit pupil of the optical system may be disposed for maximum deviation from telecentricity towards divergent chief rays.

The optical system may comprise a projection subsystem and an imaging subsystem, which may be combined into a projection/imaging system (also referred to as a projection/imaging subsystem), wherein the projection subsystem and the imaging subsystem share the one or more lenses and a same optical path between the beam splitter and the object.

The apparatus may further comprise a front tip. The optical system (projecting/imaging optics portion of the system) between the beam splitter and the front tip may be entirely integrated into the depth scanning module to be a single opto-mechanical module. The front tip may comprise a folding mirror disposed at a 45 degree to the optical axis. The depth scanning module may be configured to be movable as a unit along the optical axis for a range between 0.1 mm to 5 mm and have a depth scanning range between 5 mm to 40 mm. The front tip may have a height less than 20 mm.

In general, disclosed herein are apparatuses for confocal scanning. The apparatus may comprise illumination optics including a confocal illuminator configured to generate confocal illumination to the object. The apparatus can also comprise projecting/imaging optics configured to project light (e.g., the transparency pattern) onto an object and to image the object; the projection/imaging optics may have an optical axis. The projecting/imaging optics (a portion or subsystem of the optical system) can comprise one or more lenses and an exit pupil disposed for maximum deviation from telecentricity towards divergent chief rays. The apparatus can comprise a depth scanning module configured to be movable along the optical axis. The apparatus can comprise a beam splitter configured to transmit light beams of the confocal illuminator to the object and reflect light beams returned from the object. The apparatus can further comprise an image sensor configured to receive light beams returned from the object through the beam splitter.

Also described herein are methods for confocal three-dimensional scanning that may include activating a confocal illuminator configured to generate confocal illumination to an object, the confocal illuminator comprising a spatial pattern disposed on a transparent base and a light source configured to provide illumination to the spatial pattern. The method can comprise illuminating the spatial pattern, projecting the pattern onto an object and imaging the object using an optical system comprising one or more lenses and having an optical axis (e.g., the projection/imaging optics). The method can comprise scanning the object using a depth scanning module configured to be movable along the optical axis. The method can comprise transmitting light from the confocal illuminator through a beam splitter to the object (via the projection/imaging optics) and imaging light returning from the object using the imaging optics (e.g., again, via the projecting/imaging optics) and using the beam splitter to direct the returning light onto an image sensor.

The method can comprise using one or more spatial patterns on the transparent base that are not time varying. For example, the method can comprise using a spatial pattern in which the transparent base is bonded onto a first side of the beam splitter, wherein the image sensor is bonded to a second side of the beam splitter perpendicular to the first side to maintain stable relative position between the image sensor and the spatial pattern.

The method can include disposing an image of the light source (after passing through the transparency pattern) at an entrance pupil of the optical system. For example, the method can comprise disposing a spatial pattern at a conjugate plane of the image sensor such that a position of an image of the object is invariant to relative lateral shift of the spatial pattern to the image sensor. The method can comprise disposing an exit pupil of the optical system for maximum deviation from telecentricity towards divergent chief rays. The method can comprise scanning the object by moving the depth scanning as a unit along the optical axis for a range between 0.1 mm to 5 mm to have a depth scanning range between 5 mm to 40 mm.

As mentioned above, described herein are handheld apparatuses for confocal (three-dimensional) scanning. These apparatuses (devices, systems, etc.) may be compact and lightweight, and may include an LED based emitter providing a reduced speckle noise. These apparatuses may also be used without requiring precise alignment (pre-alignment) as needed in other systems in which an array of light spots is used to provide confocal imaging, having a maximal alignment error that is about 0.5 micrometers or less. The confocal apparatuses described herein may be operated without the need for such precise alignment, by using a continuous pattern instead of spots array. As described herein a simple transparency may replace the spot array used in other systems. In general, these apparatuses may require substantially fewer elements than prior art devices; the apparatuses described herein may eliminate the need for one or more of: laser, color capture auxiliary illumination, and light transmitting thermal defogging means. Further, the apparatuses described herein may have a reduced lens count (e.g., requiring fewer lenses, compared to the prior art). The small projection/imaging optics system may therefore allow a very compact apparatus, and in particular may be used with a small axial actuator, such as a compact voice coil motor (VCM).

The resulting optical configuration may be simpler and less sensitive to assembly error and thermal variations than prior art apparatuses. In addition, these apparatuses may be appropriate for straightforward color implementations, without the need for a separate illumination and dichroic filter.

For example, described herein are handheld apparatuses for confocal scanning that may include: a light source (e.g., one or more LEDs, including white-light LEDS, and/or a light collector and/or uniformizer); a transparency having a spatial pattern disposed thereon and configured to be illuminated by the light source; a beam splitter (e.g., a polarizing beam splitter) having a first surface and a second surface and an image sensor on the second surface; an imaging optics system (which may alternatively be referred to as a projection/imaging optics subsystem in some variations) comprising an optical gain and focusing lens and an exit pupil, the imaging optics system having an optical axis; a tip front (e.g., a hollow tip front) extending from the imaging optics system in the optical axis and comprising a fold mirror at a distal end of the hollow tip front, wherein there is no optical surface between the exit pupil and the fold mirror in the optical axis; and an axial scanner coupled to the imaging optics system and configured to move the imaging optics system in the optical axis relative to the fold mirror.

Unlike prior art apparatuses, the projection/imaging optics system may be configured to provide a deviation from telecentricity of a chief ray between the projection/imaging optics system and the fold mirror relative to a scan field size of between 3 and 10 degrees. It was previously believed (see, e.g., U.S. Pat. No. 8,878,905) that the optical system of a scanner should be substantially telecentric (e.g., having an angle of less than 3 degrees, preferably much less) in the space of the probed object (the object being scanned). In contrast, the apparatuses described herein may be non-telecentric, e.g., may deviate from telecentricity by a predetermined amount (e.g., between 3 degrees and 10 degrees, e.g., 8.5 degrees). The optical design of the apparatuses described herein may have a light source space that includes non-telecentric aperture imaging such that the entire projection/imaging optics are sufficiently compact and lightweight to be entirely translated axially (e.g., by a linear actuator/axial scanner such as VCM) to facilitate the depth scan.

For example, the apparatuses described herein may include an integrated projection/imaging optics system that is moved as a whole by the driver (axial actuator such as a VCM). This again distinguishes from other configurations in which a separate focusing element (which may form part of the imaging optics system) is moved separately from the rest of the imaging optics system. In general, the entire imaging optics system between the beam splitter and the hollow front tip is entirely integrated into a single opto-mechanical module that may be moved by the axial scanner.

In any of the apparatuses described herein, the transparency may be attached to the first surface of the beam splitter (e.g., to an external surface) and/or may be integrally formed as surface in/on the beam splitter in the optical axis. The spatial pattern on the transparency may be static or time varying; in some variations the spatial pattern is not time varying. The spatial pattern may be formed on or as part of the beam splitter or may be bonded to the first surface of the beam splitter. The transparency may be bonded onto the first surface of the beam splitter and the image sensor bonded to the second surface of the beam splitter, perpendicular to the first surface to maintain stable relative position between the image sensor and the spatial pattern. For example, the beam splitter may be a polarization sensitive beam splitter, and the transparency may be bonded onto the first surface of the beam splitter and the image sensor bonded to the second surface of the beam splitter, perpendicular to the first surface to maintain stable relative position between the image sensor and the spatial pattern.

The apparatuses (devices, systems, and in particular the hand-held scanners) and methods described herein may be particularly well suited for use as with three-dimensional scanning using structured light techniques and/or light-field technology. The patterns (static and/or time-varying) that may be used with any of these apparatuses and methods may be configured for providing structured light imaging by projecting the known pattern (e.g., grids, lines, bars, e.g., horizontal bars, arrays, etc.) and analyzing the manner in the pattern deforms when striking the target surface(s). The apparatus may calculate the depth and surface information of the object(s) in the scene. Thus, any of these apparatuses may be configured as structured light 3D scanners. In some variations the wavelengths of light used may be different, and different patterns of light may be applied corresponding to the different wavelengths. For example, visible and/or infrared light may be used. Any of these apparatuses may be configured as "invisible" or "imperceptible" structured light apparatuses, in which structured light is used simultaneously or concurrently without interfering with imaging at different frequencies. For example, infrared light and visible light may be applied and detected at high (including extremely high) frame rates that alternate between two different patterns. The patterns may be complimentary or opposite (e.g., in which the dark regions in a first pattern are illuminated in the second pattern). Different wavelengths of visible light may be used instead or in addition to infrared light.

The methods and apparatuses described herein may also or alternatively be configured as light field technology. Light field imaging (e.g., plentoptic imaging) may capture information about the light field emanating from a scene. For example, the intensity of light in a scene, and also the direction that the light rays are traveling in space. Any of the apparatuses and methods described herein may include an array of micro-lenses (e.g., placed in front of the one or more image sensors) to sense intensity, color, and directional information. In any of these apparatuses, a micro-lens array can be positioned before or behind the focal plane of the main lens(s). Alternatively or additionally, a mask (e.g., printed film mask) may be used. A patterned mask may attenuate light rays rather than bending them, and the attenuation may recoverably encode the rays on the 2D sensor. The apparatus may thus focus and capture conventional 2D photos at full sensor resolution, but the raw pixel values also hold a modulated 4D light field. The light field can be recovered by rearranging tiles of a 2D Fourier transform of sensor values into 4D planes, and computing the inverse Fourier transform. Full resolution image information can be recovered for the in-focus parts of the scene. A broadband mask may be placed at the lens, to allow refocused images at full sensor resolution to be computed for some surfaces (e.g., diffusely reflecting surfaces) including at particular wavelengths, such as near-IR. In general, the light field information may be used to estimate three-dimensional (e.g., depth) information from the image.

In any of the apparatuses described herein, the apparatus may be configured such that an image of the light source is positioned at an entrance pupil of the projection/imaging optics system. The entrance pupil may be part of the projection/imaging optics system, or may be between the projection/imaging optics system and the beam splitter, or it may be separate from the projection/imaging optics system.

The tip front may be configured to be removable from the rest of the apparatus, including a housing covering the light source, beam splitter, etc. The housing may include a handle portion with a grip and/or user interface (controls), such as buttons, switches, etc. The tip front may be hollow, particularly along the optical axis between the exit pupil of the projection/imaging optics system and the fold mirror. The tip front may be configured to snap onto the rest of the apparatus (e.g., the housing) and/or screw, friction fit, magnetically couple, etc. The tip front may be single-use or reusable, including sterilizable (e.g., autoclavable, for example, formed of a material that may be exposed to temperatures in excess of 100° C., including 121° C. or greater, without deforming or damaging after continuous exposure for greater than 15 minutes). Alternatively or additionally, these apparatuses may be configured for use with a removable/disposable sleeve that may fit over the tip front (including, in some variations but not all, over the optical exit at the distal end/side of the tip through which the teeth may be imaged).

In any of the apparatuses described herein the fold mirror may include a back heated defogging mirror. The fold mirror may redirect the optical axis of the apparatus out of a side window/exit for imaging teeth. The fold mirror may be disposed at a 45 degree to the optical axis at the distal end of the hollow front tip (or between an angle of 30° and 60°, 35° and 55°, 40° and 50°, etc.).

The entire apparatus, and/or the hollow front tip may be compact; generally having a size that is less than 140 mm×20 mm×20 mm (e.g., length, width, thickness). For example, the hollow front tip portion may be 80 mm×16 mm×16 mm or less (length, width, thickness).

In general, the projection/imaging optics system may be axially moved to scan an object. For example, the projection/imaging optics system may be configured to be movable as a unit along the optical axis for a range between 0.1 mm to 5 mm and have a depth scanning range between 5 mm to 40 mm.

As mentioned, the hollow front tip may have a height of 20 mm or less (e.g., 20 mm or less, 17 mm or less, 16 mm or less, 15 mm or less, 14 mm or less, 13 mm or less, etc.). The Field of view may be between 20×20 mm and 12×12 mm (e.g., between 18×14 mm or between 14×14 mm, etc.).

Because of the features described herein, including consolidating the spatial pattern of the transparency on the beam splitter, using an integrated projection/imaging optics system and/or having a maximum deviation (e.g., between 3-10°) from telcentricty towards divergent chief rays, the apparatus may be relatively lightweight. For example, the apparatus may have a total weight of 300 gram or less, e.g., 250 g or less, 200 g or less 180 g or less, etc.). In addition, the diameter of the projection/imaging optics may be 15 mm or less.

For example, described herein are handheld apparatuses for confocal scanning that include: a light source; a transparency having a spatial pattern disposed thereon and configured to be illuminated by the light source; a beam splitter having a first outer surface to which the transparency is attached and a second outer surface and an image sensor on the second outer surface; an integrated projection/imaging optics system comprising an optical gain and focusing lens and an exit pupil, the projection/imaging optics system having an optical axis; a hollow tip front extending from the projection/imaging optics system in the optical axis and comprising a fold mirror at a distal end of the hollow tip front, wherein there is no optical surface between the exit pupil and the fold mirror in the optical axis; and an axial scanner coupled to the projection/imaging optics system and configured to move the entire projection/imaging optics system in the optical axis relative to the fold mirror; wherein the projection/imaging optics system is configured to provide a deviation from telecentricity of a chief ray between the projection/imaging optics system and the fold mirror relative to a scan field size of between 3 and 10 degrees.

Also described herein are methods for confocal three-dimensional scanning. Any of these methods may include using any of the apparatuses described herein for scanning. For example, described herein are methods for confocal 3D scanning that include: illuminating a spatial pattern (either static or moving) on a first side of a beam splitter and projecting the spatial pattern down an optical axis, through the beam splitter, through an projection/imaging optics system (e.g., through a projection/imaging optics subsystem, such as an integrated projection/imaging optics system comprising an optical gain and focusing lens and an exit pupil), out of the exit pupil of the projection/imaging optics system, and though a tip front extending from the projection/imaging optics system to a fold mirror at a distal end of the hollow tip front, without passing through an optical surface between the exit pupil and the fold mirror in the optical axis; projecting the spatial pattern on a target (e.g., a tooth or other dental target); transmitting light (e.g., reflected light, florescent light, etc.) from the target back through the hollow tip, into the projection/imaging optics system, through the beam splitter and into an image sensor on a second side of the beam splitter; and scanning the target by axially moving the entire projection/imaging optics system in the optical axis relative to the fold mirror; wherein the projection/imaging optics system is configured to provide a deviation from telecentricity of a chief ray between the projection/imaging optics system and the fold mirror relative to a scan field size of between 3 and 10 degrees.

Scanning may be performed by moving the entire projection/imaging optics system as a unit along the optical axis, e.g., for a range between 0.1 mm to 5 mm, to scan at a depth of scanning range between 5 mm to 40 mm. Any appropriate rate of scanning may be used, including scanning at 10 Hz or greater (e.g., 15 Hz, 20 Hz, etc.).

In general, the spatial pattern may be any appropriate pattern, including patterns that are time varying or not time varying.

Illuminating the spatial pattern may comprise illuminating a transparency that is bonded onto a first side of the beam splitter. The image sensor may be bonded to a second side of the beam splitter perpendicular to the first side to maintain stable relative position between the image sensor and the spatial pattern. Any of these methods may also include disposing the spatial pattern at a conjugate plane of the image sensor such that a position of an image of the object is invariant to relative lateral shift of the spatial pattern to the image sensor.

The methods described herein may also include disposing an image of the light source at an entrance pupil of the optical system.

Any of these methods may also include disposing an exit pupil of the optical system for maximum deviation from telecentricity towards divergent chief rays.

In general, the methods described herein may include determining a confocal position by maximum correlation.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
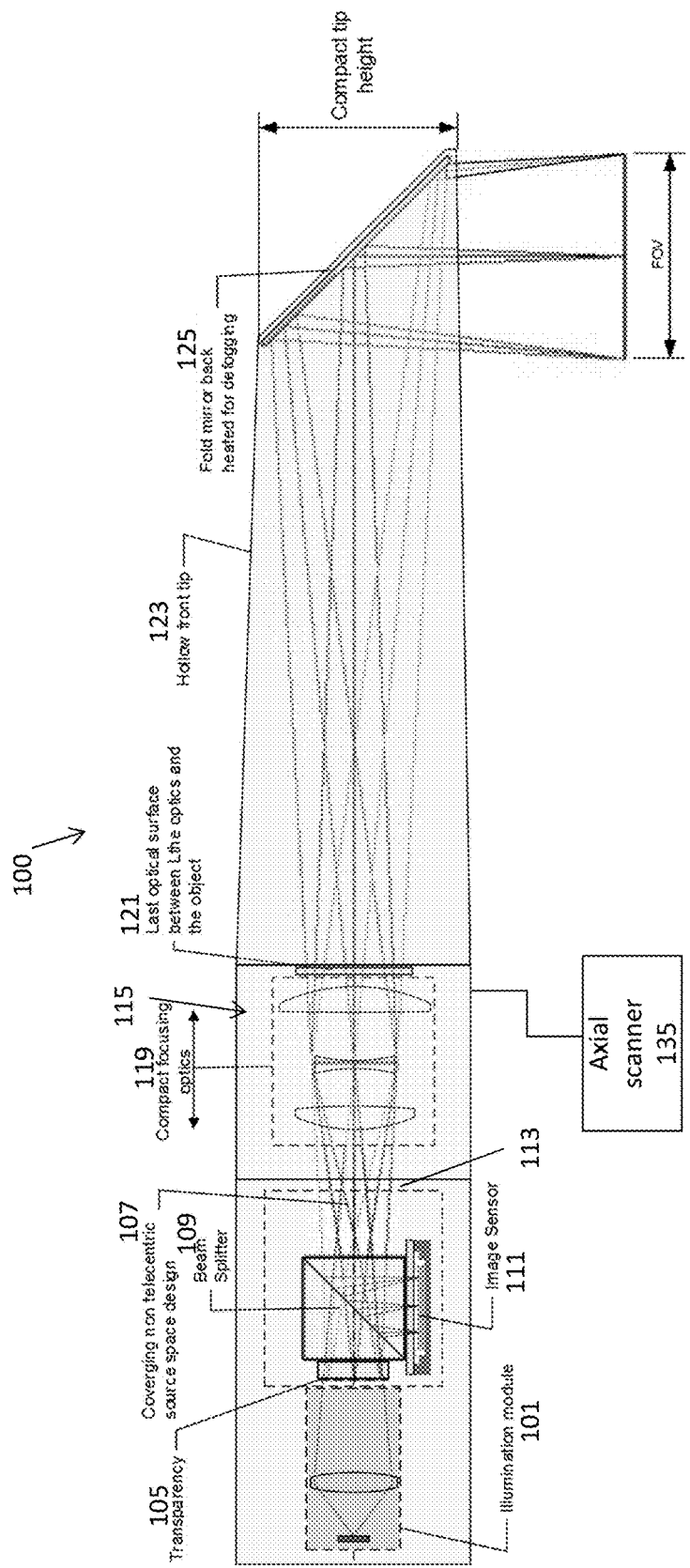
FIG. 1 schematically illustrates one example of a compact apparatus for 3D confocal scanning of an object as described herein.

The present disclosure now will be described in detail with reference to the accompanying figures. This disclosure may be embodied in many different forms and should not be construed as limited to the example embodiments discussed herein.

Described herein are compact apparatuses for confocal 3D scanning. These apparatuses can include confocal illuminator configured to generate confocal illumination to an object. The confocal illuminator can comprise a spatial pattern disposed on a transparent base (transparency) and a light source configured to provide illumination of the spatial pattern so that it can be projected onto an object. The apparatus can comprise an optical system (including projection/imaging optics) comprising one or more lenses and having an optical axis. The apparatus may also include illumination optics for illuminating a pattern/transparency forming the spatial pattern. The apparatus can comprise an axial scanner (e.g., a depth scanning module) that is configured to be move the projection/imaging optics system along the optical axis. The apparatus may include a beam splitter configured to transmit light from the light source (after passing through the pattern) to the object and reflect light returning from the object onto an imaging sensor. Thus, the apparatus may include an image sensor configured to receive light returning from the object (via the projection/imaging optics) through the beam splitter. The apparatus can be configured for 3D scanning to at least a portion of the object, for example, intraoral dental 3D scanning for all derivatives of dental restorative and orthodontics indications.

The apparatuses for confocal scanning disclosed here can include a confocal illuminator, for example, an LED illuminated transparency confocal illuminator. The apparatus can include an optical system configured project the light passing through the transparency (e.g., pattern) onto the object and image the object. The optical system may include a projection/imaging system or subsystem including projection optics and imaging optics. For example, the projection optics and the imaging optics can be configured to share the same optical elements (lenses) and the same optical path. The apparatus can comprise the depth scanning module, which comprise a compact linear actuator, for example, a voice coil motor (VCM). The apparatus can comprise a front tip, which can include a 45 degree back heated defogging fold mirror. The optical system between the beam splitter and the front tip can be configured small enough to be disposed entirely into the depth scanning module. Therefore, the apparatus confocal scanning can comprise a single opto-mechanical module for projection, imaging and depth scanning. The single optomechanical module integrating the optical system and the depth scanning module can leads to relaxed production and assembly tolerances as well as reduced manufacturing cost. The optical design may be suitable for an LED illuminated transparency, which further enables low cost manufacturing. The optical system can further therefore have a reduced lens count, for example, the optical system can comprise less than 10 lenses, less than 9 lenses, less than 5 lenses, less than 3 lenses, etc., compared to other confocal scanning systems. Furthermore, the optical system disclosed herein may be less sensitive to assembly errors and thermal variations than conventional confocal optical systems because of simpler configuration. The apparatus can comprise the optical system configured for a desired deviation from telecentricity towards divergent chief rays, for minimal front tip size. The apparatus can have a non-telecentric configuration in image and source space.

The apparatus can further comprise a polarized beam splitter as part of a confocal junction. The apparatus can be configured for drift invariant confocal conjugation. The apparatus can further support monolithic confocal conjugate assembly.

In general, these apparatuses may include an integrated projection/imaging optics system in which the entire projection/imaging optics system (e.g., the projection/imaging optics subsystem) is moved axially to scan (rather than just a focusing lens). Although moving the entire compound projection/imaging optics system in order to scan is somewhat counterintuitive, it may provide a benefit in reduced overall dimension of the apparatus, particularly in combination with the a projected spatial pattern and a configuration in which the system has a deviation from telecentricity for a chief ray between the projection/imaging optics system and the fold mirror relative to a scan field size of between 3 and 10 degrees. Because of the features described herein, these apparatuses may be more compact (e.g., 2×, 3×, or 4×) and lighter (e.g., 2× or 3×) than a typical conventional confocal scanners having the same scanning capability. For example, the apparatus can be compact and light weighted to be handheld. The apparatus can further comprise a compact high speed image sensor. The scan speed can be about 5, 10, 20, 50 scans/sec or any values therebetween. For example, the scan speed can be about 10 scans/sec.

FIG. 1 schematically illustrates one example of a compact apparatus 100 for confocal scanning of an object. The apparatus can comprise a confocal illuminator 101 (light source and/or illumination optics) configured to generate confocal illumination that may be projected onto an object. The apparatus may include a spatial pattern disposed on a transparent base, for example, a transparency 105 or a transparent glass plate. The light source and any illumination optics may be configured to provide illumination through the spatial pattern and may include a light collector/reflector. For example, the light source can be an LED light source (with, e.g., a reflector behind it to direct light through the pattern). A conventional confocal spot array light source such as laser diode can be replaced by the LED light source. For example, the apparatus can comprise an LED based emitter, which can reduce speckle noise. The spatial pattern can comprise an array of segments to achieve spot illumination. The apparatus can further comprise a light collector or a light uniformizer to create uniform illumination over the pattern. The apparatus can further comprise a condensing lens to condense light beams of the light source. The apparatus can comprise a white LED light source readily available for color model capture and rendering, which can enable straightforward color implementation.

The apparatus can comprise a beam splitter 109 and an image sensor 111. The beam splitter may be configured to transmit light beams of the confocal illuminator to the object and reflect light beams returned from the object to the image sensor. The image sensor 111 may be configured to receive light beams returned from the object. For example, the beam splitter can be a polarization beam splitter (PBS).

Figure 2:
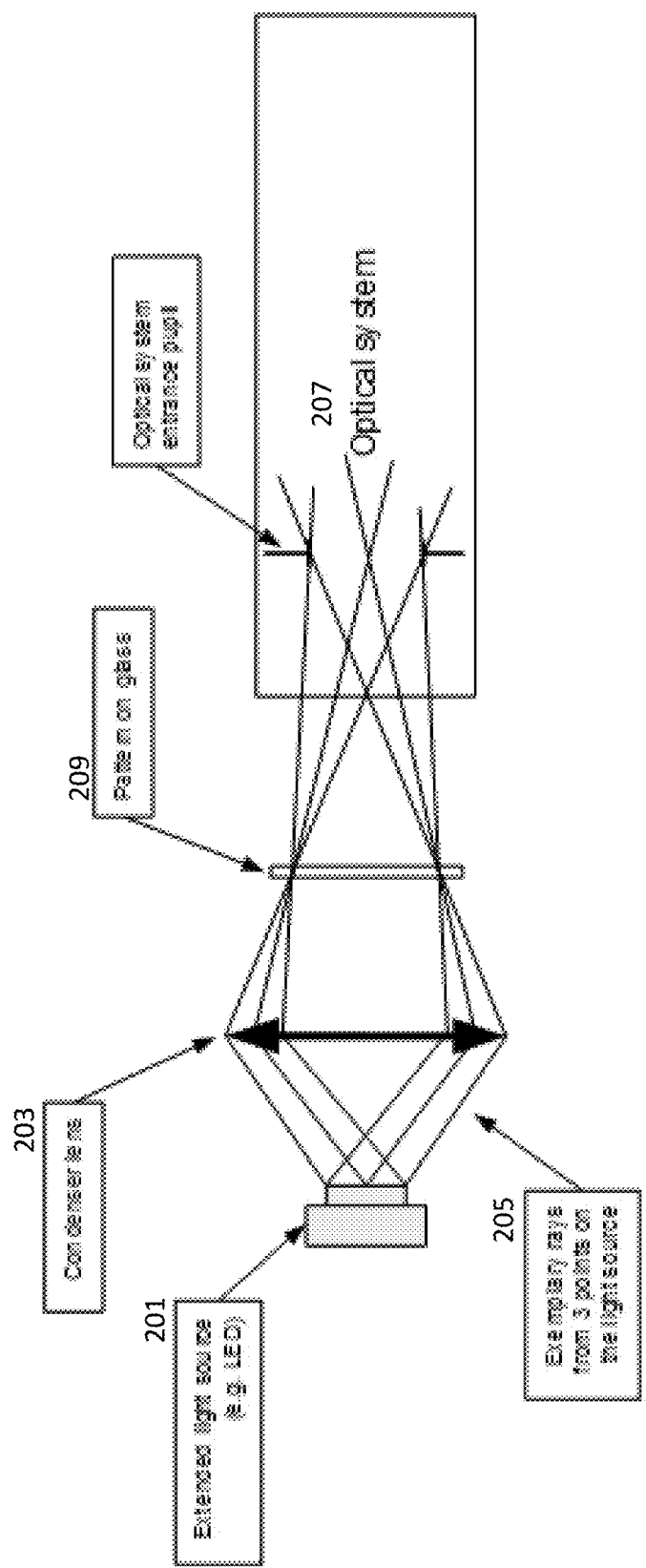
FIG. 2 schematically illustrates an example of a compact apparatus for 3D confocal scanning of an object (in this example, the light source is configured to illuminates a pattern on a transparency in Köhler illumination mode).

The apparatus can comprise an optical system (including or consisting of projection/imaging optical system/subsystem 115) comprising one or more lenses (e.g., focusing optics 119), and an exit pupil 121. The optical system can be configured to project light that passed through the transparency 105 onto the object and to image the object to the image sensor. For example, the LED light source can be configured to illuminates the transparency in Köhler illumination mode such that the image of the LED falls on the entrance pupil of the optical system, as shown in FIG. 2. Light leaving the imaging optical system 115 (including the exit pupil) may pass through a hollow front tip 123 until reaching a fold mirror 125 near the distal end of the front tip 123, and be directed out of the tip to the object (e.g., teeth); light returning from the object travels the same path. Typically, the front tip is hollow, and the entire imaging optical system moves relative to the front tip (e.g., there are no additional optical surfaces between the axially movable imaging optical system and the fold mirror in the front tip).

Referring to FIG. 2, which, like FIG. 1, shows an optical system including a light source 201 (and may also include imaging optics, such as a condenser lens 203 in this example) and an optical system 207 (e.g., which may include a projection/imaging system). For example, the illumination subsystem can be configured to illuminate the pattern (e.g., the transparency 209) and this spatial pattern 209 may be projected onto the object. The illuminated object can be imaged back through the imaging subsystem 207. The imaging subsystem can be the same as the projection/imaging subsystem between the beam splitter and the fold mirror. The imaging path and the projection path may share the same optical path and same optical elements such as the one or more lenses, as shown in FIG. 1. Thus the object can be imaged back through the same optical system and light reflected from the object can be directed onto the image sensor through the beam splitter. Unlike conventional confocal optical systems in which the imaging subsystem and the projection subsystem may be different, the apparatus for confocal scanning disclosed herein can be smaller, lighter and lower cost than the conventional confocal optical system.

Figure 3:
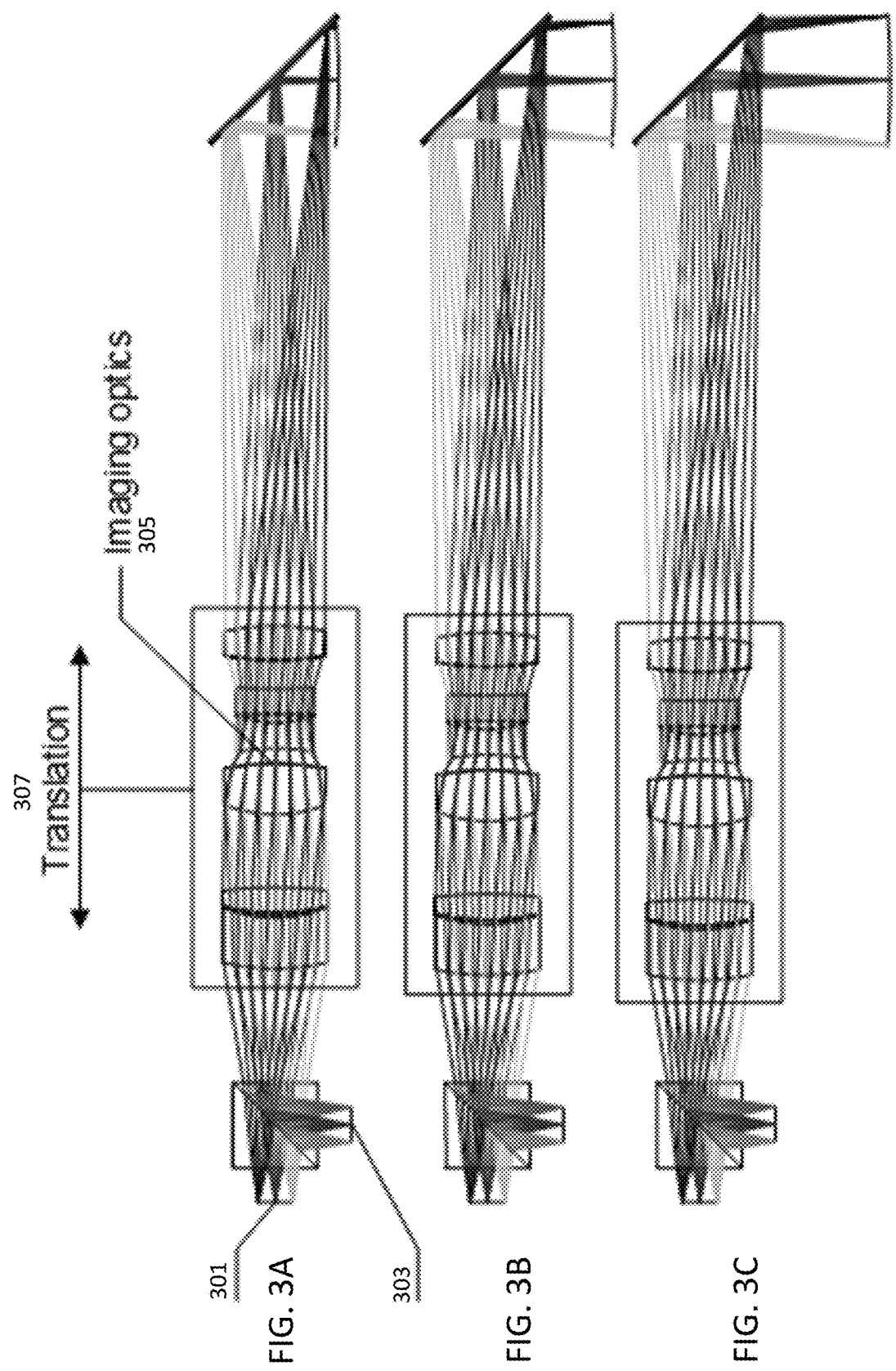
FIG. 3A schematically illustrates a depth scanning module of the apparatus for confocal scanning such as the apparatus shown in FIG. 1, in a near-focus position.
FIG. 3B schematically illustrates the depth scanning module of the apparatus for confocal scanning such as the apparatus shown in FIG. 1, in a mid-focus position.
FIG. 3C schematically illustrates the depth scanning module of the apparatus for confocal scanning such as the apparatus shown in FIG. 1, in a far-focus position.

The imaging optical system can be mounted on a depth scanning module (axial scanner 135), as shown in FIG. 1. For example, the optical system between the beam splitter and the front tip can be entirely integrated and coupled to the depth scanning module for axial movement relative to the front tip. The optical system (and in some variations the depth scanning module) can be integrated into a single optomechanical module as shown in FIG. 1, which can lead to relaxed production and assembly tolerance. The axial scanner can include a linear axial actuator which can translate the optical system axially in a controlled manner, e.g., over 0.5 to 3 mm, to facilitate depth scanning. The apparatus can be configured to have high axial magnification to enable simple depth scanning linear actuator. Axial magnification from the transparency to the object space being scanned can be between 4× to 30×, for example, between 5× to 12×. With the above translation range and magnification range, the optics periodic translation can yields object space depth scan coverage in the range of 10 mm to 36 mm. FIGS. 3A-3C schematically illustrate axially scanning of the apparatus for confocal scanning in a near-focus position (FIG. 3A), a mid-focus position (FIG. 3B) and a far-focus potion (FIT>3C) respectively, showing the translation of the entire imaging optical system 307, including projection/imaging optics 305. The projected spatial pattern 301 is transmitted onto/in the object and reflected light is received by the sensor 303 for analysis to determine the 3D surface of the object.

The optical system including the combined projection/imaging subsystem can result in simple projection optics (focus optics) and projection/imaging optics design and reduced the number of optical elements, such as optical lenses. The projection optics may refer to the same optics as the imaging optics but in the projection direction (e.g., from the light source onto the object). For example, the optical system can comprise less than 10, 9, 5, or 3 optical elements. For example, the optical lenses in the optical system can have a diameter of about 5 mm, 8 mm, 10 mm, 14 mm, 15 mm or any values therebetween, while the optical lenses in the conventional confocal optical system may have a diameter of about 25 mm. For example, the optical system disclosed herein further eliminated the following elements in a typical conventional confocal scanning apparatus such as dichroic filter, micro-lens, etc. The apparatus for confocal scanning disclosed herein is more compact, lighter weight and lower cost than a conventional confocal scanning apparatus. For example, the apparatus can have a weight of about 100, 200 or 300 grams in some embodiments. For example, the apparatus can have a size less than 150 mm×25 mm×25 mm, 140 mm×20 mm×20 mm, or 130 mm×14 mm×14 mm in some embodiments.

Figure 4:
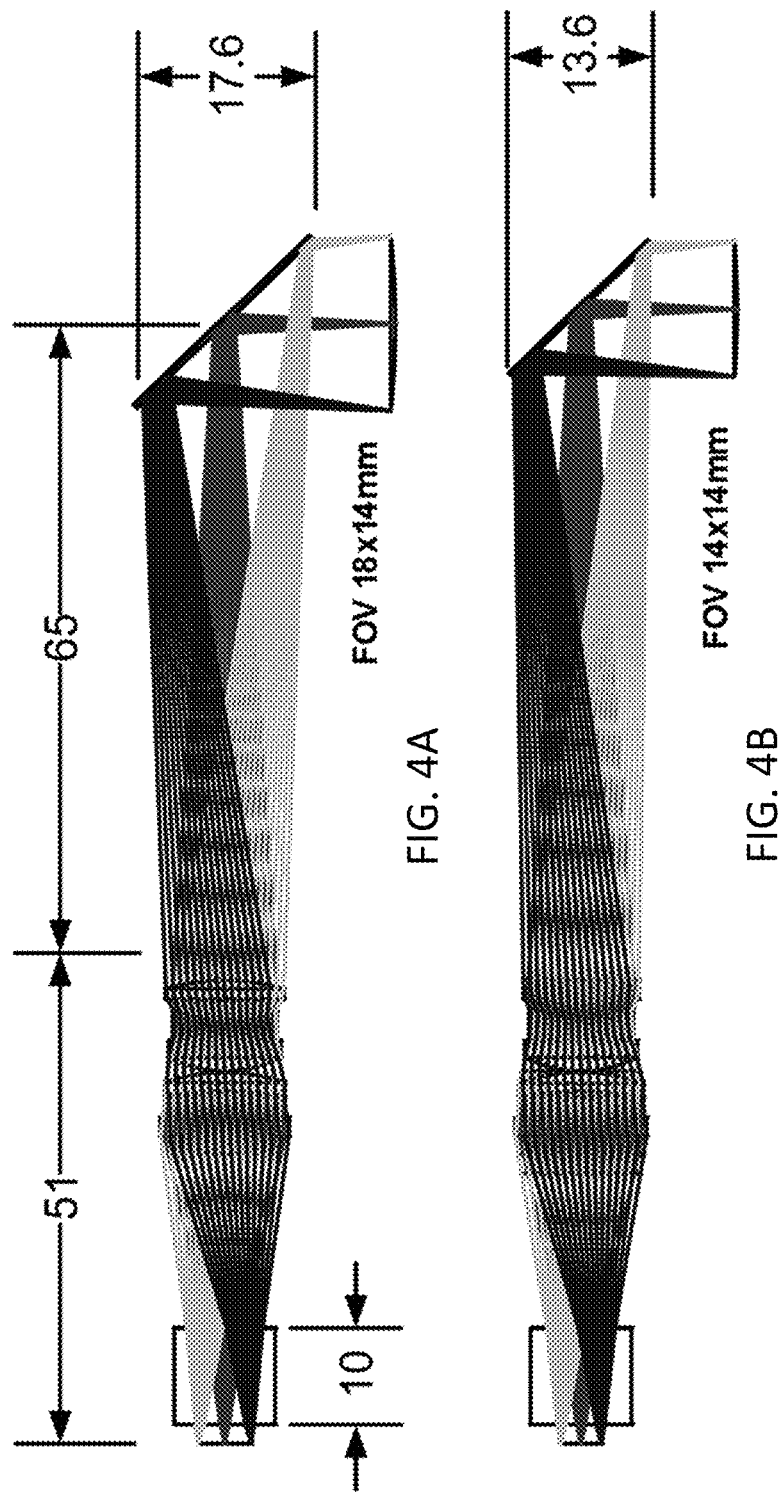
FIG. 4A illustrates an example of a compact apparatus for confocal scanning comprising a hollow front tip with a field of view (FOV) 18×14 mm, as described herein. Note that the dimensions provided are for illustrative purposes only.
FIG. 4B illustrate an example of a compact apparatus for confocal scanning comprising a hollow front tip with a field of view (FOV) 14×14 mm, as described herein. Note that the dimensions provided are for illustrative purposes only.

FIG. 4A schematically illustrates an apparatus for compact confocal scanning comprising a hollow front tip with a field of view (FOV) 18×14 mm. FIG. 4B illustrate an apparatus for compact confocal scanning comprising a hollow front tip with a field of view (FOV) 14×14 mm. As shown in FIGS. 4A and 4B, the apparatus for compact confocal scanning can have a smaller front tip size than conventional confocal scanning apparatus. The apparatus can have a front tip height of about 14 mm with a FOV of 14×14 mm. The hollow front tip can comprise a back heated defogging fold mirror. For example, the hollow tip can have a dimension of about 90 mm×20 mm×20 mm, 80 mm×16 mm×16 mm, or 60 mm×14 mm×14 mm in some embodiments. These dimensions are for illustration only; other dimensions may be used.

Figure 5:
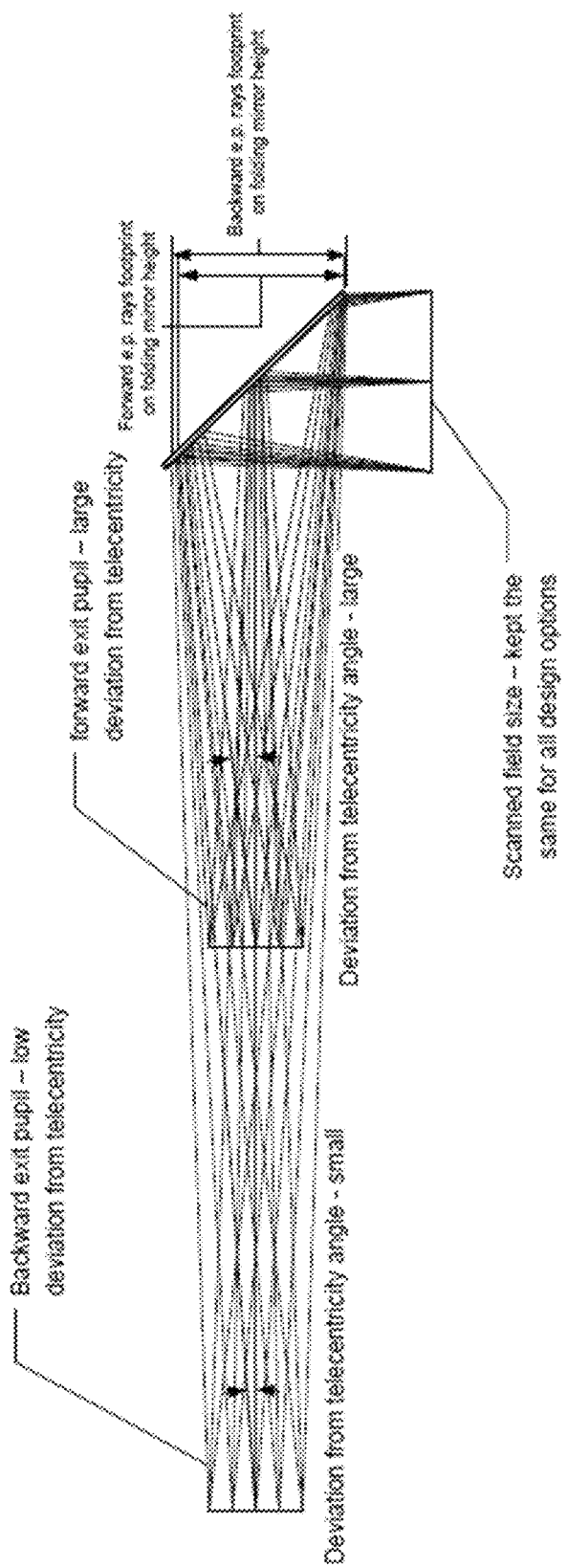
FIG. 5 schematically illustrates the non-telecentricity of an optical system as described herein for a compact apparatus for confocal 3D scanning.

In general, any of the apparatuses described herein may be non-telecentric. Specifically, the projection/imaging optics system may be configured to provide a deviation from telecentricity of a chief ray between the projection/imaging optics system and the fold mirror relative to a scan field size of between 3 and 10 degrees. FIG. 5 schematically illustrates an example of a non-telecentric optical system of an apparatus for confocal scanning in one embodiment of the disclosure. The optical system can be configured with the light source space non-telecentric aperture imaging such that the optical system is sufficiently compact and lightweight to be translated axially, for example, by a linear actuator such as a voice coil motor (VCM), to facilitate the depth scan. The exit pupil of the optical system can be located for maximum deviation from telecentricity towards divergent chief rays, which can enable minimal size of a front tip of the apparatus. The scanned field size can be the same for all design options, for a specific distance from the tip, for example, a mid-range of a scan depth. The deviation angle from telecentricity can be determined by the exit pupil distance from the object focus and the field size. The tip height can be derived by the footprint of the beams of the light source on the folding mirror. This height can be smaller as the exit pupil gets closer to the object focus (forward exit pupil). Possible range of deviation angle from telecentricity can be from about 3 degrees to about 10 degrees. For example, the deviation angle from telecentricity can be about 8.5 degrees in some embodiments. The deviation angle from telecentricity is for the field extent in the mirror folding plane, which has effect on the tip height.

Figure 6:
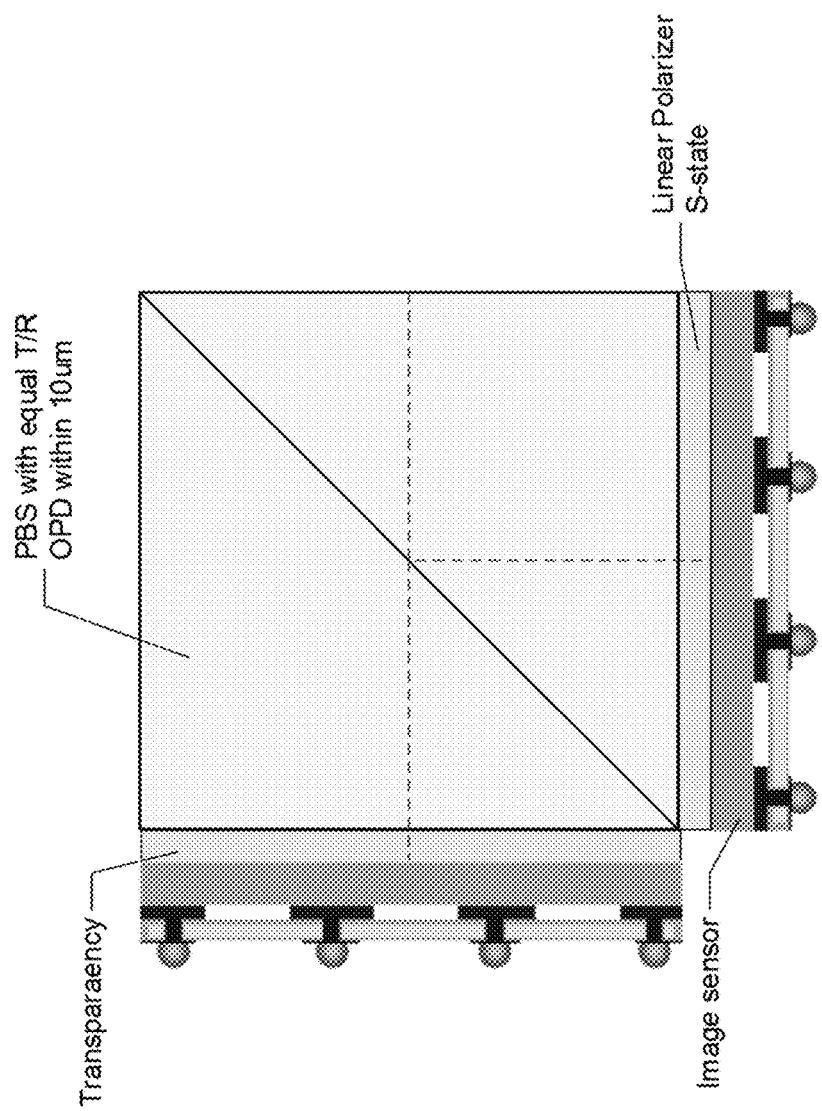
FIG. 6 schematically illustrates an example of a confocal focal plane module of an apparatus for confocal scanning where a transparency and image sensor are bonded directly to a beam splitter or mounted on a fixture relative to the beam splitter.

FIG. 6 schematically illustrates an example of a confocal illuminator of an apparatus for confocal scanning where a transparency (including a spatial pattern) is bonded directly to a beam splitter or mounted on a fixture relative to the beam splitter in one embodiment. The transparency can be bonded directly onto one facet the beam splitter, for example, onto a first surface of a beam splitter (e.g., Polarizing Beam Splitter, PBS) while the image sensor can be bonded onto another facet (e.g., a second surface) of the beam splitter perpendicular to the transparency, thus maintaining stable relative position ("confocal condition") between the image sensor and the transparency as shown in FIG. 6. The apparatus can be configured for drift invariant confocal conjugation. The transparency and the image sensor can be disposed on conjugate planes of the object. The apparatus can further support monolithic confocal conjugate assembly. Pattern based illumination enables conjugate imaging onto the image sensor, which is invariant to relative lateral shift. The apparatus for confocal scanning can be configured to have position invariant correlation, which may be less sensitive to assembly drift.

Figure 7B:
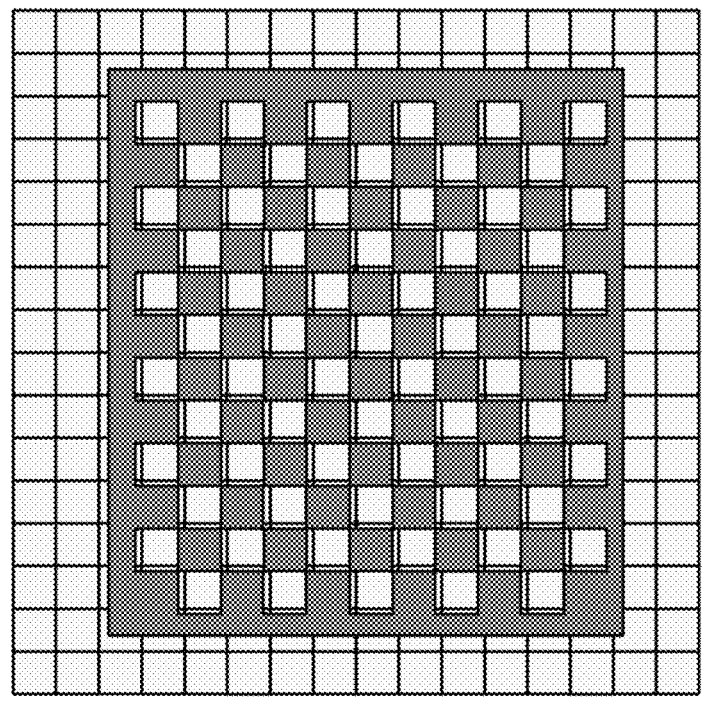
FIG. 7B illustrates an example of an ordered spatial pattern that may be used as part of a compact apparatus for 3D confocal scanning as described herein.
Figure 7A:
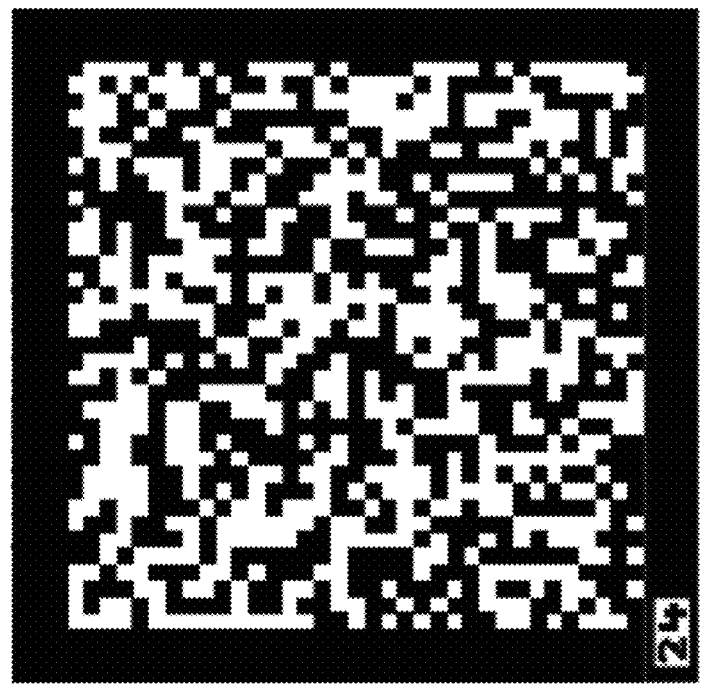
FIG. 7A illustrates an example of a disordered spatial pattern that may be used as part of a compact apparatus for 3D confocal scanning as described herein.

FIGS. 7A and 7B illustrates examples of spatial patterns that may be used as part of any of the compact apparatuses for 3D confocal scanning described herein. FIG. 7A illustrates an example of a disordered pattern of an apparatus for confocal scanning. FIG. 7B illustrates an example of an ordered pattern of an apparatus for confocal scanning. The apparatus for confocal scanning can comprise an illuminated pattern to replace an array of light beams in a conventional confocal scanning apparatus. For example, a white LED back illuminated pattern can be used to achieve confocal imaging. A variety of patterns can be used in the confocal illuminator, which enables design flexibility and lower signal requirement. For example, the pattern can comprise an array of segments to achieve spot-illumination equivalent. The illumination spots through the pattern can be nearly diffraction limited. For example, the pattern can comprise an array of segments that have a size similar to pinholes in a conventional confocal microscope. For example, the pattern can comprise an array of segments that have a diameter of about 1 µm, 10 µm, 25 µm, 50 µm, 1 mm or 2 mm or any values therebetween.

For example, the apparatus for confocal scanning can further comprise an array of detection pinholes. For example, the detection pinholes can be disposed in a fixture between the beam splitter and the image sensor. For example, the detection pinholes can be bonded or integrated in the image sensor. For example, the size of the pinholes can be configured adapted to the numerical aperture (NA) of the optical system and the wavelength of the light source. For example, the size of the detection pinholes can be further adapted to a magnification of the optical system.

The confocal position can be determination by maximum correlation. For example, a reference pattern position can be invariant. For example, a depth position per pixel or a group of pixels of the image sensor can be assigned corresponding to the maximum signal obtained on the pixel or the group of pixels following a depth scan. Lateral resolution need not be compromised because all pixels within region of interest (ROI) can be used. For example, resolution can be improved by sub-pixel processing Also described herein are methods for confocal 3D confocal three-dimensional scanning dimensional scanning. In general, the method can comprise activating a confocal illuminator configured to generate confocal illumination to an object. The method can comprise using the confocal illuminator comprising a spatial pattern disposed on a transparent base and a light source configured to provide illumination to the spatial pattern, and/or any additional illumination optics (e.g., lenses).

The method can comprise illuminating a pattern, projecting the pattern onto an object, and imaging the object by an optical system comprising projecting/imaging optics including one or more lenses and having an optical axis. The method can comprise scanning the object by a depth scanning module configured to be movable along the optical axis. The method can comprise projecting beams of light from the confocal illuminator through a beam splitter, onto the object, and directing light returning from the object onto an imaging sensor using the beam splitter.

For example, the method can comprise using a spatial pattern on the transparent base that is not time varying. For example, the method can comprise using the spatial pattern and the transparent base, wherein the pattern (e.g., a transparency) is bonded onto a first side of the beam splitter, further wherein the image sensor is bonded to a second side of the beam splitter perpendicular to the first side to maintain stable relative position between the image sensor and the spatial pattern.

A method can comprise disposing an image of the light source at an entrance pupil of the optical system. For example, the method can comprise disposing the spatial pattern at a conjugate plane of the image sensor such that a position of an image of the object is invariant to relative lateral shift of the spatial pattern to the image sensor. For example, the method can comprise disposing an exit pupil of the optical system for maximum deviation from telecentricity towards divergent chief rays.

A method can comprise disposing scanning the object comprises moving the depth scanning as a unit along the optical axis for a range between 0.1 mm to 5 mm to have a depth scanning range between 5 mm to 40 mm. For example, the method can comprise determining a confocal position by maximum correlation.

As discussed briefly above, the apparatuses and methods described herein may also be configured as structured light scanning systems and/or light-field 3D reconstruction systems. For example, in some variations light field data may be captured, for example, by including configuring the imaging system as a plenotoptic apparatus, for example, by including a plurality of micro-lenses before or after the focal plane of the main lensing sub-system (e.g., the compact focusing optics). Thus, in some variations the light may pass through an optical surface (the micro-lenses) between the exit pupil and the fold mirror in the optical axis alternatively, the micro-lenses may from part of the compact focusing optics. A depth map may be created from the light field data, and this depth map may8 be used to create surfaces. Traditional stereo imaging methods may be used for depth map extraction, or depth data may be extracted from light field cameras by combining two or more methods of depth estimation.

Figure 8:
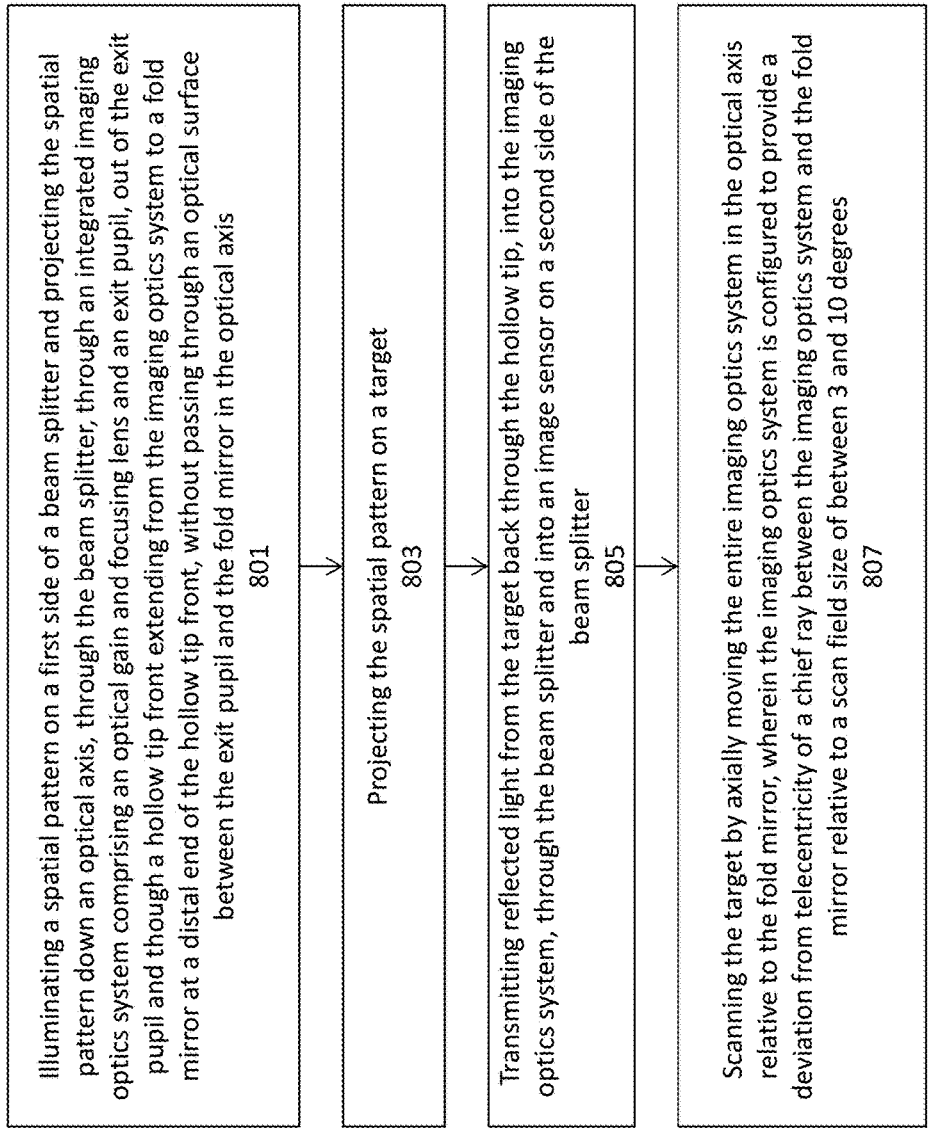
FIG. 8 illustrates an example of a method for confocal three-dimensional scanning as described herein.

FIG. 8 illustrates another example of a method as described herein. in FIG. 8, the method for confocal three-dimensional scanning, includes first illuminating a spatial pattern on a first side of a beam splitter and projecting the spatial pattern down an optical axis, through the beam splitter, through an integrated projection/imaging optics system comprising an optical gain and focusing lens and an exit pupil, out of the exit pupil and though a hollow tip front extending from the projection/imaging optics system to a fold mirror at a distal end of the hollow tip front, without passing through an optical surface between the exit pupil and the fold mirror in the optical axis 801. The method then includes projecting the spatial pattern on a target 803 and transmitting reflected light from the target back through the hollow tip, into the projection/imaging optics system, through the beam splitter and into an image sensor on a second side of the beam splitter 805. The method may also include scanning the target by axially moving the entire projection/imaging optics system in the optical axis relative to the fold mirror 807, wherein the projection/imaging optics system is configured to provide a deviation from telecentricity of a chief ray between the projection/imaging optics system and the fold mirror relative to a scan field size of between 3 and 10 degrees.

The systems, devices, and methods of the preferred embodiments and variations thereof can be embodied and/or implemented at least in part as a machine configured to receive a computer-readable medium storing computer-readable instructions. The instructions are preferably executed by computer-executable components preferably integrated with the system including the computing device configured with software. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims. The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A handheld apparatus for scanning, the handheld apparatus comprising:
    a light source;
    a transparency having a spatial pattern disposed thereon and configured to be illuminated by the light source;
    a beam splitter having a first surface and a second surface and an image sensor on the second surface, wherein the transparency is bonded onto the first surface of the beam splitter and the image sensor is bonded to the second surface of the beam splitter perpendicular to the first surface to maintain stable relative position between the image sensor and the spatial pattern;
    a projection/imaging optics system that is non-telecentric, comprising focusing optics and an exit pupil, the projection/imaging optics system having an optical axis;
    a front tip extending from the projection/imaging optics system in the optical axis and comprising a fold mirror at a distal end of the front tip, wherein the projection/imaging optics provide a deviation from telecentricity of a chief ray between the projection/imaging optics system and the fold mirror relative to a scan field size of 3 degrees or more; and
    an axial actuator coupled to the projection/imaging optics system and configured to move the projection/imaging optics system in the optical axis relative to the fold mirror.

2. The apparatus of claim 1, wherein the projection/imaging optics system is configured to provide a deviation from telecentricity of a chief ray between the projection/imaging optics system and the fold mirror relative to a scan field size of between 3 and 10 degrees.

3. The apparatus of claim 1, wherein the transparency is attached to the first surface of the beam splitter.

4. The apparatus of claim 1, wherein the spatial pattern on the transparency is not time varying.

5. The apparatus of claim 1, wherein the beam splitter comprises a polarization sensitive beam splitter.

6. The apparatus of claim 1, wherein the apparatus is configured such that an image of the light source is positioned at an entrance pupil of the projection/imaging optics system.

7. The apparatus of claim 1, wherein the front tip is configured to be removable and autoclavable.

8. The apparatus of claim 1, wherein the projection/imaging optics system between the beam splitter and the front tip is entirely integrated into a single opto-mechanical module that is moveable by the axial actuator.

9. The apparatus of claim 1, wherein the front tip has a size less than 140 mm×20 mm×20 mm.

10. The apparatus of claim 1, wherein the fold mirror is disposed at a 45 degree angle to the optical axis at the distal end of the front tip.

11. The apparatus of claim 1, wherein the projection/imaging optics system is configured to be movable as a unit along the optical axis for a range between 0.1 mm to 5 mm and have a depth scanning range between 5 mm to 40 mm.

12. The apparatus of claim 1, wherein the front tip has a height of 20 mm or less.

13. The apparatus of claim 1, wherein the handheld apparatus has a weight of 300 gram or less.

14. The apparatus of claim 1, wherein the fold mirror comprises a back heated defogging mirror.

15. The apparatus of claim 1, wherein a diameter of the projection/imaging optics system in the optical axis is 15 mm or less.

16. The apparatus of claim 1, wherein a last optical surface from the focusing optics is a quarter waveplate (QWP).

17. A handheld apparatus for intraoral scanning, the handheld apparatus comprising:
a light source;
a transparency having a spatial pattern disposed thereon and configured to be illuminated by the light source;
a beam splitter having a first outer surface to which the transparency is attached and a second outer surface and an image sensor on the second outer surface;
a single moveable opto-mechanical module comprising an integrated projection/imaging optics system comprising focusing optics and an exit pupil, the projection/imaging optics system having an optical axis, wherein the projection/imaging optics system of the handheld apparatus is entirely integrated into the single moveable opto-mechanical module;
a hollow front tip extending from the projection/imaging optics system in the optical axis and comprising a fold mirror at a distal end of the hollow front tip, wherein there is no optical surface between the exit pupil and the fold mirror in the optical axis; and
an axial scanner coupled to the projection/imaging optics system and configured to move the single moveable opto-mechanical module comprising an entirety of the projection/imaging optics system in the optical axis relative to the fold mirror;
wherein the projection/imaging optics system is configured to provide a deviation from telecentricity of a chief ray between the projection/imaging optics system and the fold mirror relative to a scan field size of between 3 and 10 degrees.

18. The apparatus of claim 17, wherein the spatial pattern on the transparency is not time varying.

19. The apparatus of claim 17, wherein the beam splitter comprise a polarization sensitive beam splitter, and wherein the transparency is bonded onto the first outer surface of the beam splitter and the image sensor is bonded to the second outer surface of the beam splitter perpendicular to the first outer surface to maintain a stable relative position between the image sensor and the spatial pattern.

20. The apparatus of claim 17, wherein the apparatus is configured such that an image of the light source is positioned at an entrance pupil of the projection/imaging optics system.

21. The apparatus of claim 17, wherein the hollow front tip is configured to be removable and autoclavable.

22. The apparatus of claim 17, wherein the hollow front tip has a size less than 140 mm×20 mm×20 mm.

23. The apparatus of claim 17, wherein the hollow front tip has a size of 80 mm×16 mm×16 mm or less.

24. The apparatus of claim 17, wherein the fold mirror is disposed at a 45 degree to the optical axis at the distal end of the hollow front tip.

25. The apparatus of claim 17, wherein the projection/imaging optics system is configured to be movable as a unit along the optical axis for a range between 0.1 mm to 5 mm and have a depth scanning range between 5 mm to 40 mm.

26. The apparatus of claim 17, wherein the hollow front tip has a height of 20 mm or less.

27. The apparatus of claim 17, wherein the apparatus has a weight of 300 gram or less.

28. The apparatus of claim 17, wherein the fold mirror comprises a back heated defogging mirror.

29. The apparatus of claim 17, wherein a diameter of the projection/imaging optics system in the optical axis is 15 mm or less.

30. A method for three-dimensional scanning, the method comprising:
illuminating a spatial pattern on a first side of a beam splitter and projecting the spatial pattern down an optical axis, through the beam splitter, through a projection/imaging optics system comprising focusing optics and an exit pupil, out of the exit pupil and though a hollow front tip extending from the projection/imaging optics system to a fold mirror at a distal end of the hollow front tip, without passing through an optical surface between the exit pupil and the fold mirror in the optical axis, wherein illuminating the spatial pattern comprises illuminating at least a part of a transparency that is bonded onto a first side of the beam splitter;
projecting the spatial pattern on a target;
transmitting reflected light from the target back through the hollow tip, into the projection/imaging optics system, through the beam splitter and into an image sensor on a second side of the beam splitter, wherein the image sensor is bonded to a second side of the beam splitter perpendicular to the first side to maintain stable relative position between the image sensor and the spatial pattern; and
scanning the target by axially moving at least a portion of the projection/imaging optics system in the optical axis relative to the fold mirror.

31. The method of claim 30, wherein scanning comprises scanning at 10 Hz or greater.

32. The method of claim 30, wherein illumining the spatial pattern comprises illuminating a spatial pattern that is not time varying.

33. The method of claim 30, further comprising disposing an image of a light source at an entrance pupil of the optical system.

34. The method of claim 30, further comprising disposing the spatial pattern at a conjugate plane of the image sensor such that a position of an image of the target is invariant to relative lateral shift of the spatial pattern to the image sensor.

35. The method of claim 30, further comprising disposing an exit pupil of the projection/imaging optical optics system for a substantial deviation from telecentricity towards divergent chief rays.

36. The method of claim 30, wherein scanning the target comprises moving the entire projection/imaging optics system as a unit along the optical axis for a range between 0.1 mm to 5 mm to have a depth scanning range between 5 mm to 40 mm.

37. The method of claim 30, further comprising determining a confocal position by maximum correlation.

38. A method for three-dimensional scanning of teeth in a patient's mouth, the method comprising:
illuminating a spatial pattern on a first side of a beam splitter and projecting the spatial pattern down an optical axis, through the beam splitter, through an integrated projection/imaging optics system comprising focusing optics and an exit pupil, out of the exit pupil and though a hollow front tip extending from the projection/imaging optics system to a fold mirror at a distal end of the hollow front tip, without passing through an optical surface between the exit pupil and the fold mirror in the optical axis, wherein the projection/imaging optics system is entirely integrated into a single moveable opto-mechanical module;

projecting the spatial pattern on a target;

transmitting reflected light from the target back through the hollow tip, into the projection/imaging optics system, through the beam splitter and into an image sensor on a second side of the beam splitter; and scanning the target by axially moving the single moveable opto-mechanical module comprising an entirety of the projection/imaging optics system in the optical axis relative to the fold mirror;

wherein the projection/imaging optics system is configured to provide a deviation from telecentricity of a chief ray between the projection/imaging optics system and the fold mirror relative to a scan field size of between 3 and 10 degrees.

39. The method of claim 38, wherein the scanning comprises scanning at 10 Hz or greater.

40. The method of claim 38, wherein illumining the spatial pattern comprises illuminating a spatial pattern that is not time varying.

41. The method of claim 38, wherein illuminating the spatial pattern comprises illuminating at least a part of a transparency that is bonded onto a first side of the beam splitter, further wherein the image sensor is bonded to a second side of the beam splitter perpendicular to the first side to maintain stable relative position between the image sensor and the spatial pattern.

42. The method of claim 38, further comprising disposing an image of a light source at an entrance pupil of the optical system.

43. The method of claim 38, further comprising disposing the spatial pattern at a conjugate plane of the image sensor such that a position of an image of the target is invariant to relative lateral shift of the spatial pattern to the image sensor.

44. The method of claim 38, further comprising disposing an exit pupil of the projection/imaging optical system for a substantial deviation from telecentricity towards divergent chief rays.

45. The method of claim 38, wherein scanning the target comprises moving the entire projection/imaging optics system as a unit along the optical axis for a range between 0.1 mm to 5 mm to have a depth scanning range between 5 mm to 40 mm.

46. The method of claim 38, further comprising determining a confocal position by maximum correlation.

* * * * *